(12) United States Patent
Hoey et al.

(10) Patent No.: US 11,331,135 B2
(45) Date of Patent: May 17, 2022

(54) SYSTEMS AND METHODS FOR PROSTATE TREATMENT

(71) Applicant: Boston Scientific Scimed, Inc., Maple Grove, MN (US)

(72) Inventors: Michael Hoey, Shoreview, MN (US); John H. Shadduck, Menlo Park, CA (US)

(73) Assignee: BOSTON SCIENTIFIC SCIMED, INC., Maple Grove, MN (US)

( * ) Notice: Subject to any disclaimer, the term of this patent is extended or adjusted under 35 U.S.C. 154(b) by 353 days.

(21) Appl. No.: 16/510,022

(22) Filed: Jul. 12, 2019

(65) Prior Publication Data
US 2020/0008858 A1    Jan. 9, 2020

Related U.S. Application Data

(63) Continuation of application No. 12/843,581, filed on Jul. 26, 2010, now Pat. No. 10,390,873, which is a (Continued)

(51) Int. Cl.
*A61B 18/14* (2006.01)
*A61B 18/04* (2006.01)
*A61B 18/00* (2006.01)

(52) U.S. Cl.
CPC .... *A61B 18/04* (2013.01); *A61B 2018/00017* (2013.01); *A61B 2018/00029* (2013.01); (Continued)

(58) Field of Classification Search
CPC .......... A61B 18/04; A61B 2018/00017; A61B 2018/00547; A61B 2018/00577; A61B 2218/005; A61B 2018/1475
See application file for complete search history.

(56) References Cited

U.S. PATENT DOCUMENTS

| 408,899 A | 8/1889 | Small |
| 1,719,750 A | 7/1929 | Bridge et al. |
| (Continued) | | |

FOREIGN PATENT DOCUMENTS

| CM | 101803947 A | 8/2010 |
| CN | 2061443 U | 9/1990 |
| (Continued) | | |

OTHER PUBLICATIONS

US 5,326,343 A, 07/1994, Rudie et al. (withdrawn)
(Continued)

*Primary Examiner* — Jaymi E Della
(74) *Attorney, Agent, or Firm* — Bookoff McAndrews, PLLC

(57) ABSTRACT

An energy delivery probe is provided that may include any of a number of features. One feature of the energy delivery probe is that it can apply energy to tissue, such as a prostrate, to shrink, damage, denaturate the prostate. In some embodiments, the energy can be applied with a vapor media. The energy delivery probe can include a vapor delivery member configured to extend into a transition zone prostate tissue. A condensable vapor media can be delivered from the vapor delivery member into the transition zone tissue, wherein the condensable vapor media can propagate interstitially in the transition zone tissue and be confined in the transition zone tissue by boundary tissue adjacent to the transition zone tissue. Methods associated with use of the energy delivery probe are also covered.

19 Claims, 15 Drawing Sheets

Related U.S. Application Data continuation of application No. 12/768,544, filed on Apr. 27, 2010, now Pat. No. 9,833,277.

(60) Provisional application No. 61/173,108, filed on Apr. 27, 2009.

(52) U.S. Cl.
CPC ............ *A61B 2018/00547* (2013.01); *A61B 2018/00577* (2013.01); *A61B 2018/1425* (2013.01); *A61B 2218/005* (2013.01)

(56) References Cited

U.S. PATENT DOCUMENTS

| | | | |
|---|---|---|---|
| 4,672,963 A | 6/1987 | Barken | |
| 4,920,982 A | 5/1990 | Goldstein | |
| 4,950,267 A | 8/1990 | Ishihara et al. | |
| 5,117,482 A | 5/1992 | Hauber | |
| 5,222,185 A | 6/1993 | McCord, Jr. | |
| 5,249,585 A | 10/1993 | Turner et al. | |
| 5,300,099 A | 4/1994 | Rudie | |
| 5,312,399 A | 5/1994 | Hakky et al. | |
| 5,330,518 A | 7/1994 | Neilson et al. | |
| 5,366,490 A | 11/1994 | Edwards et al. | |
| 5,370,609 A | 12/1994 | Drasler et al. | |
| 5,370,675 A | 12/1994 | Edwards et al. | |
| 5,370,677 A | 12/1994 | Rudie et al. | |
| 5,385,544 A | 1/1995 | Edwards et al. | |
| 5,409,453 A | 4/1995 | Lundquist et al. | |
| 5,413,588 A | 5/1995 | Rudie et al. | |
| 5,421,819 A | 6/1995 | Edwards et al. | |
| 5,435,805 A * | 7/1995 | Edwards | A61N 1/06 604/22 |
| 5,464,437 A | 11/1995 | Reid et al. | |
| 5,470,308 A | 11/1995 | Edwards et al. | |
| 5,470,309 A | 11/1995 | Edwards et al. | |
| 5,484,400 A | 1/1996 | Edwards et al. | |
| 5,499,998 A | 3/1996 | Meade | |
| 5,531,676 A | 7/1996 | Edwards et al. | |
| 5,531,763 A | 7/1996 | Mastri et al. | |
| 5,542,915 A | 8/1996 | Edwards et al. | |
| 5,542,916 A | 8/1996 | Hirsch et al. | |
| 5,545,171 A | 8/1996 | Sharkey et al. | |
| 5,549,644 A | 8/1996 | Lundquist et al. | |
| 5,554,110 A | 9/1996 | Edwards et al. | |
| 5,556,377 A | 9/1996 | Rosen et al. | |
| 5,558,673 A | 9/1996 | Edwards et al. | |
| 5,588,960 A | 12/1996 | Edwards et al. | |
| 5,591,125 A | 1/1997 | Edwards et al. | |
| 5,599,294 A | 2/1997 | Edwards et al. | |
| 5,601,591 A | 2/1997 | Edwards et al. | |
| 5,628,770 A | 5/1997 | Thome et al. | |
| 5,630,794 A | 5/1997 | Lax et al. | |
| 5,645,528 A | 7/1997 | Thome | |
| 5,667,488 A | 9/1997 | Lundquist et al. | |
| 5,672,153 A | 9/1997 | Lax et al. | |
| 5,709,680 A | 1/1998 | Yates et al. | |
| 5,720,718 A | 2/1998 | Rosen et al. | |
| 5,720,719 A | 2/1998 | Edwards et al. | |
| 5,776,176 A | 7/1998 | Rudie | |
| 5,792,070 A | 8/1998 | Kauphusman et al. | |
| 5,797,903 A | 8/1998 | Swanson et al. | |
| 5,800,486 A | 9/1998 | Thome et al. | |
| 5,807,395 A | 9/1998 | Mulier et al. | |
| 5,830,179 A | 11/1998 | Mikus et al. | |
| 5,843,144 A | 12/1998 | Rudie et al. | |
| 5,849,011 A | 12/1998 | Jones et al. | |
| 5,861,021 A | 1/1999 | Thome et al. | |
| 5,871,481 A | 2/1999 | Kannenberg et al. | |
| 5,873,877 A | 2/1999 | McGaffigan et al. | |
| 5,897,553 A | 4/1999 | Mulier et al. | |
| 5,899,932 A | 5/1999 | Dann et al. | |
| 5,938,692 A | 8/1999 | Rudie | |
| 5,944,715 A | 8/1999 | Goble et al. | |
| 5,951,515 A | 9/1999 | Osterlind | |
| 5,957,922 A | 9/1999 | Imran | |
| 5,964,752 A | 10/1999 | Stone | |
| 5,964,756 A | 10/1999 | McGaffigan et al. | |
| 5,976,123 A | 11/1999 | Baumgardner et al. | |
| 5,987,360 A | 11/1999 | McGrath et al. | |
| 5,990,465 A | 11/1999 | Nakaoka et al. | |
| 6,007,571 A | 12/1999 | Neilson et al. | |
| 6,009,351 A | 12/1999 | Flachman | |
| 6,017,358 A | 1/2000 | Yoon et al. | |
| 6,017,361 A | 1/2000 | Mikus | |
| 6,036,631 A | 3/2000 | McGrath et al. | |
| 6,036,713 A | 3/2000 | Kieturakis | |
| 6,053,909 A | 4/2000 | Shadduck | |
| 6,063,081 A | 5/2000 | Mulier et al. | |
| 6,067,475 A | 5/2000 | Graves et al. | |
| 6,077,257 A | 6/2000 | Edwards et al. | |
| 6,113,593 A | 9/2000 | Tu et al. | |
| 6,122,551 A | 9/2000 | Rudie et al. | |
| 6,123,083 A | 9/2000 | McGrath | |
| 6,147,336 A | 11/2000 | Oshijima et al. | |
| 6,148,236 A | 11/2000 | Dann | |
| 6,156,036 A | 12/2000 | Sussman et al. | |
| 6,161,049 A | 12/2000 | Rudie et al. | |
| 6,179,805 B1 | 1/2001 | Sussman et al. | |
| 6,179,836 B1 | 1/2001 | Eggers et al. | |
| 6,206,847 B1 | 3/2001 | Edwards et al. | |
| 6,210,404 B1 | 4/2001 | Shadduck | |
| 6,223,085 B1 | 4/2001 | Dann et al. | |
| 6,231,591 B1 | 5/2001 | Desa | |
| 6,235,022 B1 | 5/2001 | Hallock et al. | |
| 6,238,389 B1 | 5/2001 | Paddock et al. | |
| 6,238,391 B1 | 5/2001 | Olsen et al. | |
| 6,238,393 B1 | 5/2001 | Mulier et al. | |
| 6,241,702 B1 | 6/2001 | Lundquist et al. | |
| 6,258,087 B1 | 7/2001 | Edwards et al. | |
| 6,272,384 B1 | 8/2001 | Simon et al. | |
| 6,287,297 B1 | 9/2001 | Woodruff et al. | |
| 6,302,903 B1 | 10/2001 | Mulier et al. | |
| 6,312,391 B1 | 11/2001 | Ramadhyani et al. | |
| 6,315,777 B1 | 11/2001 | Comben | |
| 6,348,039 B1 | 2/2002 | Flachman et al. | |
| 6,387,093 B1 * | 5/2002 | Ellman | A61B 18/1482 128/898 |
| 6,398,759 B1 | 6/2002 | Sussman et al. | |
| 6,409,722 B1 | 6/2002 | Hoey et al. | |
| 6,423,027 B1 | 7/2002 | Gonon | |
| 6,440,127 B2 | 8/2002 | McGovern et al. | |
| 6,461,296 B1 | 10/2002 | Desai | |
| 6,494,902 B2 | 12/2002 | Hoey et al. | |
| 6,496,737 B2 | 12/2002 | Rudie et al. | |
| 6,508,816 B2 | 1/2003 | Shadduck | |
| 6,517,534 B1 | 2/2003 | McGovern et al. | |
| 6,524,270 B1 | 2/2003 | Bolmsjo et al. | |
| 6,537,248 B2 | 3/2003 | Mulier et al. | |
| 6,537,272 B2 | 3/2003 | Christopherson et al. | |
| 6,544,211 B1 | 4/2003 | Andrew et al. | |
| 6,551,300 B1 | 4/2003 | McGaffigan | |
| 6,565,561 B1 | 5/2003 | Goble et al. | |
| 6,575,929 B2 | 6/2003 | Sussman et al. | |
| 6,575,968 B1 | 6/2003 | Eggers et al. | |
| 6,579,270 B2 | 6/2003 | Sussman et al. | |
| 6,589,201 B1 | 7/2003 | Sussman et al. | |
| 6,607,529 B1 | 8/2003 | Jones et al. | |
| 6,638,275 B1 * | 10/2003 | McGaffigan | A61B 18/1477 606/41 |
| 6,640,139 B1 | 10/2003 | Ueberle | |
| 6,669,694 B2 | 12/2003 | Shadduck | |
| 6,676,628 B2 | 1/2004 | Sussman et al. | |
| 6,706,039 B2 | 3/2004 | Muller et al. | |
| 6,716,252 B2 | 4/2004 | Lazarovitz et al. | |
| 6,719,738 B2 | 4/2004 | Mehier | |
| 6,726,696 B1 | 4/2004 | Houser et al. | |
| 6,730,079 B2 | 5/2004 | Lovewell | |
| 6,736,810 B2 | 5/2004 | Hoey et al. | |
| 6,740,108 B1 | 5/2004 | Just et al. | |
| 6,760,616 B2 | 7/2004 | Hoey et al. | |
| 6,780,178 B2 | 8/2004 | Palanker et al. | |
| 6,827,718 B2 | 12/2004 | Hutchins et al. | |

(56) References Cited

U.S. PATENT DOCUMENTS

| | | |
|---|---|---|
| 6,855,141 B2 | 2/2005 | Lovewell |
| 6,887,237 B2 | 5/2005 | McGaffigan |
| 6,905,475 B2 | 6/2005 | Hauschild et al. |
| 6,911,028 B2 | 6/2005 | Shadduck |
| 6,969,376 B2 | 11/2005 | Takagi et al. |
| 6,974,455 B2 | 12/2005 | Garabedian et al. |
| 7,014,652 B2 | 3/2006 | Cioanta et al. |
| 7,041,121 B1 | 5/2006 | Williams et al. |
| 7,066,935 B2 | 6/2006 | Swoyer et al. |
| 7,089,064 B2 | 8/2006 | Manker et al. |
| 7,130,697 B2 | 10/2006 | Chornenky et al. |
| 7,238,182 B2 | 7/2007 | Swoyer et al. |
| 7,247,155 B2 | 7/2007 | Hoey et al. |
| 7,261,709 B2 | 8/2007 | Swoyer et al. |
| 7,261,710 B2 | 8/2007 | Elmouelhi et al. |
| 7,322,974 B2 | 1/2008 | Swoyer et al. |
| 7,328,068 B2 | 2/2008 | Spinelli et al. |
| 7,328,069 B2 | 2/2008 | Gerber |
| 7,335,197 B2 | 2/2008 | Sage et al. |
| 7,340,300 B2 | 3/2008 | Christopherson et al. |
| 7,369,894 B2 | 5/2008 | Gerber |
| 7,429,262 B2 | 9/2008 | Woloszko et al. |
| 7,437,194 B2 | 10/2008 | Skwarek et al. |
| 7,470,228 B2 | 12/2008 | Connors et al. |
| 7,549,987 B2 | 6/2009 | Shadduck |
| 7,865,250 B2 | 1/2011 | Mrva et al. |
| 7,894,913 B2 | 2/2011 | Boggs et al. |
| 7,959,577 B2 | 6/2011 | Schmitz et al. |
| 8,048,069 B2 | 11/2011 | Skwarek et al. |
| 8,216,217 B2 | 7/2012 | Sharkey et al. |
| 8,244,327 B2 | 8/2012 | Fichtinger et al. |
| 8,301,264 B2 | 10/2012 | Achenbach et al. |
| 8,313,485 B2 | 11/2012 | Shadduck |
| 8,409,109 B2 | 4/2013 | Tiesma et al. |
| 8,550,743 B2 | 10/2013 | Bonde et al. |
| 8,585,692 B2 | 11/2013 | Shadduck et al. |
| 8,740,957 B2 | 6/2014 | Masotti |
| 8,900,223 B2 | 12/2014 | Shadduck |
| 9,345,507 B2 | 5/2016 | Hoey et al. |
| 9,968,395 B2 | 5/2018 | Hoey et al. |
| 2002/0078956 A1 | 6/2002 | Sharpe et al. |
| 2002/0111617 A1 | 8/2002 | Cosman et al. |
| 2002/0177846 A1* | 11/2002 | Mulier ............... A61B 18/04 606/27 |
| 2003/0069575 A1 | 4/2003 | Chin et al. |
| 2003/0092689 A1 | 5/2003 | Escandon et al. |
| 2003/0097126 A1 | 5/2003 | Woloszko et al. |
| 2003/0130575 A1 | 7/2003 | Desai |
| 2003/0206730 A1 | 11/2003 | Golan |
| 2003/0216759 A1* | 11/2003 | Burbank ............... A61B 8/0833 606/157 |
| 2004/0006334 A1 | 1/2004 | Beyar et al. |
| 2004/0068306 A1 | 4/2004 | Shadduck |
| 2004/0186422 A1 | 9/2004 | Rioux et al. |
| 2004/0225286 A1* | 11/2004 | Elliott ............... A61B 17/12136 606/41 |
| 2004/0230316 A1 | 11/2004 | Cioanta et al. |
| 2004/0267340 A1 | 12/2004 | Cioanta et al. |
| 2005/0010203 A1 | 1/2005 | Edwards et al. |
| 2005/0096629 A1 | 5/2005 | Gerber et al. |
| 2005/0124915 A1 | 6/2005 | Eggers et al. |
| 2005/0149020 A1 | 7/2005 | Jahng |
| 2005/0159676 A1 | 7/2005 | Taylor et al. |
| 2006/0089636 A1 | 4/2006 | Christopherson et al. |
| 2006/0135955 A1 | 6/2006 | Shadduck |
| 2006/0178670 A1 | 8/2006 | Woloszko et al. |
| 2006/0224154 A1 | 10/2006 | Shadduck et al. |
| 2006/0224169 A1 | 10/2006 | Weisenburgh, II et al. |
| 2006/0253069 A1 | 11/2006 | Li et al. |
| 2006/0276871 A1 | 12/2006 | Lamson et al. |
| 2007/0032785 A1 | 2/2007 | Diederich et al. |
| 2007/0038039 A1 | 2/2007 | Adler et al. |
| 2007/0142846 A1 | 6/2007 | Catanese, III et al. |
| 2007/0179491 A1 | 8/2007 | Kratoska et al. |
| 2007/0197864 A1 | 8/2007 | Dejima et al. |
| 2007/0213703 A1 | 9/2007 | Naam et al. |
| 2008/0021484 A1 | 1/2008 | Catanese, III et al. |
| 2008/0021485 A1 | 1/2008 | Catanese, III et al. |
| 2008/0033232 A1 | 2/2008 | Catanese, III et al. |
| 2008/0033458 A1 | 2/2008 | McLean et al. |
| 2008/0033488 A1 | 2/2008 | Catanese, III et al. |
| 2008/0039833 A1 | 2/2008 | Catanese, III et al. |
| 2008/0039872 A1 | 2/2008 | Catanese, III et al. |
| 2008/0039874 A1 | 2/2008 | Catanese, III et al. |
| 2008/0039875 A1 | 2/2008 | Catanese, III et al. |
| 2008/0039876 A1 | 2/2008 | Catanese, III et al. |
| 2008/0039893 A1 | 2/2008 | McLean et al. |
| 2008/0039894 A1 | 2/2008 | Catanese et al. |
| 2008/0046045 A1 | 2/2008 | Yon et al. |
| 2008/0110457 A1 | 5/2008 | Barry et al. |
| 2008/0132826 A1 | 6/2008 | Shadduck et al. |
| 2008/0188811 A1 | 8/2008 | Kim |
| 2008/0208187 A1 | 8/2008 | Bhushan et al. |
| 2008/0214956 A1 | 9/2008 | Briggs et al. |
| 2008/0217325 A1 | 9/2008 | Von Buren et al. |
| 2008/0249399 A1 | 10/2008 | Appling et al. |
| 2008/0262491 A1 | 10/2008 | Swoyer et al. |
| 2008/0269737 A1 | 10/2008 | Elmouelhi et al. |
| 2008/0269862 A1 | 10/2008 | Elmouelhi et al. |
| 2008/0275440 A1 | 11/2008 | Kratoska et al. |
| 2008/0297287 A1 | 12/2008 | Shachar et al. |
| 2008/0312497 A1 | 12/2008 | Elmouelhi et al. |
| 2009/0018553 A1 | 1/2009 | McLean et al. |
| 2009/0054871 A1 | 2/2009 | Sharkey et al. |
| 2009/0138001 A1 | 5/2009 | Barry et al. |
| 2009/0149846 A1 | 6/2009 | Hoey et al. |
| 2009/0199855 A1 | 8/2009 | Davenport |
| 2009/0216220 A1 | 8/2009 | Hoey et al. |
| 2009/0227998 A1 | 9/2009 | Aljuri et al. |
| 2009/0277457 A1 | 11/2009 | Hoey et al. |
| 2009/0306640 A1 | 12/2009 | Glaze et al. |
| 2010/0016757 A1 | 1/2010 | Greenburg et al. |
| 2010/0049031 A1 | 2/2010 | Fruland et al. |
| 2010/0094270 A1 | 4/2010 | Sharma |
| 2010/0114083 A1 | 5/2010 | Sharma |
| 2010/0145254 A1 | 6/2010 | Shadduck et al. |
| 2010/0145325 A1 | 6/2010 | Shadduck et al. |
| 2010/0145326 A1 | 6/2010 | Hoey et al. |
| 2010/0179416 A1 | 7/2010 | Hoey et al. |
| 2010/0179528 A1 | 7/2010 | Shadduck et al. |
| 2010/0193568 A1 | 8/2010 | Scheib et al. |
| 2010/0204688 A1 | 8/2010 | Hoey et al. |
| 2010/0256636 A1 | 10/2010 | Fernandez et al. |
| 2010/0262133 A1 | 10/2010 | Hoey et al. |
| 2010/0262137 A1 | 10/2010 | Nye et al. |
| 2011/0077628 A1 | 3/2011 | Hoey et al. |
| 2011/0106072 A1 | 5/2011 | Sundquist et al. |
| 2011/0160648 A1 | 6/2011 | Hoey |
| 2011/0264176 A1 | 10/2011 | Jackson et al. |
| 2011/0319759 A1 | 12/2011 | Liu et al. |
| 2012/0259271 A1 | 10/2012 | Shadduck et al. |
| 2013/0006231 A1 | 1/2013 | Sharma et al. |
| 2013/0074847 A1 | 3/2013 | Hoey et al. |
| 2014/0200568 A1 | 7/2014 | Sharma |
| 2015/0025515 A1 | 1/2015 | Hoey et al. |
| 2015/0126990 A1 | 5/2015 | Sharma et al. |
| 2016/0015445 A1 | 1/2016 | Hoey et al. |
| 2016/0081736 A1 | 3/2016 | Hoey et al. |
| 2016/0220296 A1 | 8/2016 | Hastings et al. |
| 2016/0270838 A1 | 9/2016 | Hastings et al. |
| 2016/0331435 A1 | 11/2016 | Hoey et al. |
| 2017/0056089 A1 | 3/2017 | Hoey et al. |
| 2018/0168711 A1 | 6/2018 | Hoey et al. |
| 2018/0168712 A1 | 6/2018 | Hoey et al. |
| 2018/0193080 A1 | 7/2018 | Hoey et al. |

FOREIGN PATENT DOCUMENTS

| | | |
|---|---|---|
| CN | 2418844 Y | 2/2001 |
| CN | 101072544 A | 11/2007 |
| CN | 101257855 A | 9/2008 |
| CN | 101006939 A | 11/2008 |
| CN | 101491458 A | 7/2009 |
| CN | 101803947 A | 8/2010 |

(56) References Cited

FOREIGN PATENT DOCUMENTS

| | | |
|---|---|---|
| JP | 7-507696 A | 8/1995 |
| JP | 8-501957 A | 3/1996 |
| JP | 8-504613 A | 5/1996 |
| JP | 11-318925 A | 11/1999 |
| JP | 2000-14663 A | 1/2000 |
| JP | 2000005191 A | 1/2000 |
| JP | 2001-500763 A | 1/2001 |
| JP | 2005137916 A | 6/2005 |
| WO | 92/10142 A1 | 6/1995 |
| WO | 01/24715 A1 | 4/2001 |
| WO | 03/088851 A1 | 10/2003 |
| WO | 03/096871 A2 | 11/2003 |
| WO | 2005/102416 A1 | 11/2005 |
| WO | 2006/004482 A1 | 1/2006 |
| WO | 2008/083407 A1 | 7/2008 |
| WO | 2010/080467 A2 | 7/2010 |
| WO | 2017/106843 A1 | 6/2017 |

OTHER PUBLICATIONS

Hoey et al.; U.S. Appl. No. 14/106,388 entitled "Systems and Methods for Prostate Treatment," filed Dec. 13, 2014.

Hoey et al.; U.S. Appl. No. 14/241,977 entitled "Systems and Methods for Prostate Treatment," filed Feb. 28, 2014.

Hoey et al.; U.S. Appl. No. 12/614,218 entitled "Systems and Methods for Treatment of Prostatic Tissue," filed Nov. 6, 2009.

Hoey et al.; U.S. Appl. No. 12/768,544 entitled "Systems and Methods for Prostate Treatment," filed Apr. 27, 2010.

Hoey et al.; U.S. Appl. No. 12/768,558 entitled "Systems and Methods for Prostate Treatment," filed Apr. 27, 2010.

Hai; Photoselective Vaporization Prostatectomy: A Palliative Treatment Option for Men with Urinary Obstruction Secondary to Prostate Cancer: PCRI Prost. Cancer Rsrch. Inst. Reprint.from PCRI Insights Nov. 2005, vol. 8(4); Dwnld from http://www.prostate-cancer.org/pcricms/node/233 on May 10, 12; 4 pages.

Hoey et al.; U.S. Appl. No. 13/764,645 entitled "Systems and Methods for Treatment of BPH," filed Feb. 11, 2013.

Shadduck et al.; U.S. Appl. No. 13/779,616 entitled "Systems and Methods for Treatment of Prostatic Tissue," filed Feb. 27, 2013.

Hoey et al.; U.S. Appl. No. 13/595,914 entitled "Systems and Methods for Treatment of Prostatic Tissue," filed Aug. 27, 2012.

Hoey et al.; U.S. Appl. No. 13/072,573 entitled "Systems and Methods for Prostate Treatment," filed Mar. 25, 2011.

Hoey et al.; U.S. Appl. No. 13/626,657 entitled "Systems and Methods for Male Sterilization," filed Sep. 25, 2012.

Hoey et al.; U.S. Appl. No. 13/352,198 entitled "Systems and methods for prostate treatment," filed Jan. 17, 2012.

\* cited by examiner

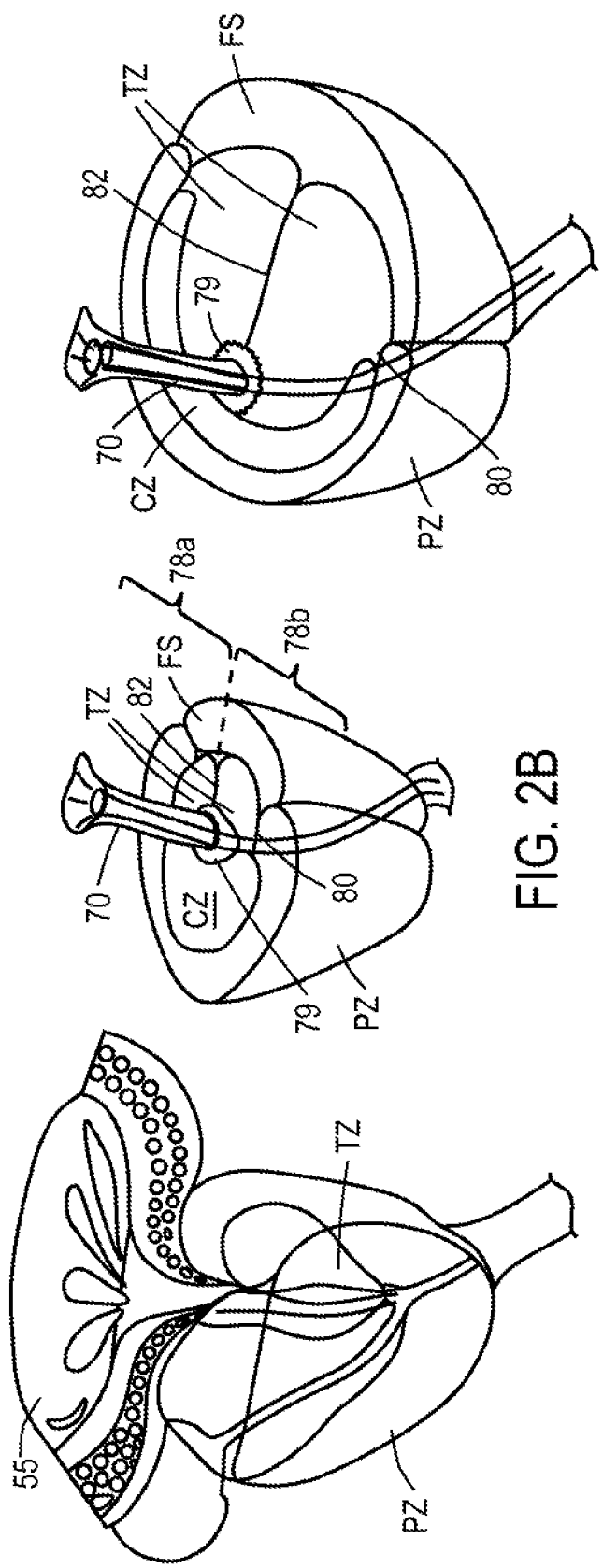

SYSTEMS AND METHODS FOR PROSTATE TREATMENT

CROSS-REFERENCE TO RELATED APPLICATIONS

This application is a continuation of U.S. application Ser. No. 12/843,581, filed Jul. 26, 2010, which is a continuation of U.S. application Ser. No. 12/768,544, filed Apr. 27, 2010, now U.S. Pat. No. 9,833,277, issued on Dec. 5, 2017, which claims the benefit under 35 U.S.C. § 119 of U.S. Provisional Patent Application No. 61/173,108, filed Apr. 27, 2009. These applications are each herein incorporated by reference in their entireties.

INCORPORATION BY REFERENCE

All publications, including patents and patent applications, mentioned in this specification are herein incorporated by reference in their entirety to the same extent as if each individual publication was specifically and individually indicated to be incorporated by reference.

FIELD OF THE INVENTION

The present invention relates to devices and related methods for treatment of benign prostatic hyperplasia using a minimally invasive approach.

BACKGROUND OF THE INVENTION

Benign prostatic hyperplasia (BPH) is a common disorder in middle-aged and older men, with prevalence increasing with age. At age 70, more than one-half of men have symptomatic BPH, and nearly 90% of men have microscopic evidence of an enlarged prostate. The severity of symptoms also increase with age with 27% of patients in the 60-70 age bracket having moderate-to-severe symptoms, and 37% of patients in their 70's suffering from moderate-to-severe symptoms.

The prostate gland early in life is the size and shape of a walnut and weighs about 20 grams. Prostate enlargement appears to be a normal process. With age, the prostate gradually increases in size to twice or more its normal size. The fibromuscular tissue of the outer prostatic capsule restricts expansion after the gland reaches a certain size. Because of such restriction on expansion, the intracapsular tissue will compress against and constrict the prostatic urethra thus causing resistance to urine flow.

FIG. 1 is a sectional schematic view the male urogenital anatomy, with the walnut-sized prostate gland 50 located below the bladder 55 and bladder neck indicated at 56. The walls 58 of bladder 55 can expand and contract to cause urine flow through the urethra 60, which extends from the bladder 55, through the prostate 50 and penis 62. The portion of urethra 60 that is surrounded by the prostate gland 50 is referred to as the prostatic urethra 70. The prostate 50 also surrounds the ejaculatory ducts 72 which have an open termination in the prostatic urethra 70. During sexual arousal, sperm is transported from the testes 74 by the ductus deferens 76 to the prostate 50 which provides fluids that combine with sperm to form semen during ejaculation. On each side of the prostate, the ductus deferens 76 and seminal vesicles 77 join to form a single tube called an ejaculatory duct 72. Thus, each ejaculatory duct 72 carries the seminal vesicle secretions and sperm into the prostatic urethra 70.

Referring to FIGS. 2A-2B and 3, the prostate glandular structure can be classified into three zones: the peripheral zone PZ, transition zone TZ, and central zone CZ. FIGS. 2A and 2B illustrate a normal prostate gland, and FIG. 3 schematically depicts an enlarged prostate resulting from benign prostatic hyperplasia. FIGS. 2A-2B and 3 include reference to other male anatomy as previously described with respect to FIG. 1. In a normal prostate as depicted in FIGS. 2A-2B, the peripheral zone PZ, which is the region forming the postero-inferior aspect of the gland, contains 70% of the prostate glandular elements. A majority of prostate cancers (up to 80%) arise in the peripheral zone tissue PZ. The central zone CZ surrounds the ejaculatory ducts 72 and contains about 20-25% of the prostate volume in a normal prostate. The central zone is often the site of inflammatory processes. The transition zone TZ is the site in which benign prostatic hyperplasia develops, and contains about 5-10% of the volume of glandular elements in a normal prostate (FIGS. 2A, 2B). Referring to FIG. 3, the peripheral zone tissue PZ can constitute up to 80% of prostate such volume in a case of BPH. The transition zone TZ consists of two lateral prostate lobes 78a, 78b and the periurethral region indicated at 79. As can be understood from FIGS. 2B-3, there are natural barriers around the transition zone tissue TZ, namely, the prostatic urethra 70, the anterior fibromuscular stroma FS, and a fibrous plane 80 between the transition zone TZ and peripheral zone PZ. Another fibrous plane 82 lies between the lobes 78a and 78b. In FIGS. 2A-3, the anterior fibromuscular stroma FS or fibromuscular zone can be seen which is predominantly fibromuscular tissue.

BPH is typically diagnosed when the patient seeks medical treatment complaining of bothersome urinary difficulties. The predominant symptoms of BPH are an increase in frequency and urgency of urination. BPH can also cause urinary retention in the bladder which in turn can lead to lower urinary tract infection (LUTI). In many cases, the LUTI then can ascend into the kidneys and cause chronic pyelonephritis, and can eventually lead to renal insufficiency. BPH also may lead to sexual dysfunction related to sleep disturbance or psychological anxiety caused by severe urinary difficulties. Thus, BPH can significantly alter the quality of life with aging of the male population.

BPH is the result of an imbalance between the continuous production and natural death (apoptosis) of the glandular cells of the prostate. The overproduction of such cells leads to increased prostate size, most significantly in the transition zone TZ which traverses the prostatic urethra (FIG. 3).

In early stage cases of BPH, drug treatments can alleviate the symptoms. For example, alpha-blockers treat BPH by relaxing smooth muscle tissue found in the prostate and the bladder neck, which may allow urine to flow out of the bladder more easily. Such drugs can prove effective until the glandular elements cause overwhelming cell growth in the prostate.

More advanced stages of BPH, however, can only be treated by surgical interventions. A number of methods have been developed using electrosurgical or mechanical extraction of tissue, and thermal ablation or cryoablation of intracapsular prostatic tissue. In many cases, such interventions provide only transient relief, and there often is significant peri-operative discomfort and morbidity.

In one prior art ablation method for treating BPH, an RF needle is inserted into the prostate and RF energy is delivered to prostate tissue. In a first aspect of the prior art system and method, the elongated RF needle can be extended from an introducer member into the prostate lobes from the urethra. Some prior art systems further utilize an insulator sleeve extended over the RF needle through the urethral wall to prevent thermal damage to the urethra. The resulting RF treatment thus ablates tissue regions away from the prostatic urethra and purposefully does not target tissue close to and parallel to, the prostatic urethra. The prior art systems and method leave an untreated tissue region around the urethra in which smooth muscle cells and alpha adrenergic receptors are not ablated. Thus, the untreated tissue can continue to compress the urethra and subsequent growth of such undamaged tissue can expand into the outwardly ablated regions.

In another aspect of some prior art RF methods, the application of RF energy typically extends for 2 to 3 minutes or longer which can allow thermal diffusion of the ablation to reach the capsule periphery of the prostate. In some instances, the application of RF energy for such a long duration can cause lesions that extend beyond the prostate and into the urethra. Such prior art RF energy delivery methods may not create a durable effect, since smooth muscle tissue and are not uniformly ablated around the prostatic urethra. Due to the size of lesions created with RF ablation, these prior art systems typically ablate at a suboptimal location within the prostate (e.g., at a distance of 2 cm or greater from the prostatic urethra) to prevent damage to this tissue. The result can be leaving non-ablated tissue adjacent the urethra that may once again be subject to hyperplasia. As a result, the hyperplasia in the lobes can continue resulting in tissue impinging on the urethra thus limiting long term effectiveness of the RF ablation treatment.

SUMMARY OF THE INVENTION

A method for treating benign prostatic hyperplasia (BPH) is provided, comprising introducing a vapor delivery member into a transition zone tissue of a prostate, and injecting a condensable vapor media from the vapor delivery member into the transition zone tissue, wherein the condensable vapor media propagates interstitially in the transition zone tissue and is confined in the transition zone tissue by a boundary tissue adjacent the transition zone tissue.

In some embodiments, the boundary tissue comprises a prostatic urethra. In other embodiments, the boundary tissue comprises a fibrous plane between lateral lobes of the prostate. In other embodiments, the boundary tissue comprises a central zone tissue. In yet additional embodiments, the boundary tissue comprises a fibrous plane between transition zone tissue and a peripheral zone tissue. In one embodiment, the boundary tissue comprises an anterior fibromuscular stromal tissue.

In some embodiments, the condensable vapor media is injected for an interval of 20 second or less. In another embodiment, the condensable vapor media is injected at a pressure at the tissue interface ranging from about 20 mm Hg to 200 mm Hg.

In some embodiments, the vapor deliver member is introduced transversely relative to a urethra. In another embodiment, the vapor deliver member is introduced substantially aligned with a urethra.

In some embodiments, the condensable vapor media is injected in a plurality of selected locations in the transition zone tissue.

In one embodiment, the vapor delivery member is introduced into the transition zone tissue through a wall of a urethra from a trans-urethral probe. In another embodiment, the vapor delivery member is introduced into the transition zone tissue from a trans-rectal probe.

In some embodiments, a pressure of the vapor media introduction is controlled by a computer controller.

A method for treating benign prostatic hyperplasia (BPH) is provided, comprising introducing a probe into a prostatic urethra, extending a vapor delivery member from the probe into a transition zone tissue of a prostate at a depth of less than 12 mm outward from the prostatic urethra, and delivering a condensable vapor media from the vapor delivery member to the transition zone tissue.

In some embodiments, the condensable vapor media is delivered into the transition zone tissue for a delivery interval of less than 20 seconds. In other embodiments, the condensable vapor media is delivered into the transition zone tissue for a delivery interval of less than 10 seconds.

In some embodiments, the condensable vapor media is delivered into the transition zone tissue at a delivery pressure ranging from approximately 20 mm Hg to 200 mm Hg. In other embodiments, the condensable vapor media is configured to provide energy ranging from 1 to 40 cal/sec into the transition zone tissue.

A method for treating benign prostatic hyperplasia (BPH) is provided, comprising introducing a vapor delivery member into at least one selected location in transition zone tissue of a prostate, and injecting a condensable vapor media from the vapor delivery member into the transition zone tissue so as to ablate transition zone tissue adjacent a urethra without ablating transition zone tissue adjacent a fibromuscular stroma.

BRIEF DESCRIPTION OF THE DRAWINGS

FIG. 2A is a perspective view of a patient's normal prostate showing zones of prostate tissue.

FIG. 2B is transverse sectional view of the normal prostate of FIG. 2A showing tissue zones, including the central zone, the transition zone, the peripheral zone and the fibromuscular stroma.

FIG. 3 is another sectional view of a patient prostate later in life with BPH greatly increasing the dimensions of the transition zone.

DETAILED DESCRIPTION OF THE INVENTION

Figure 4:
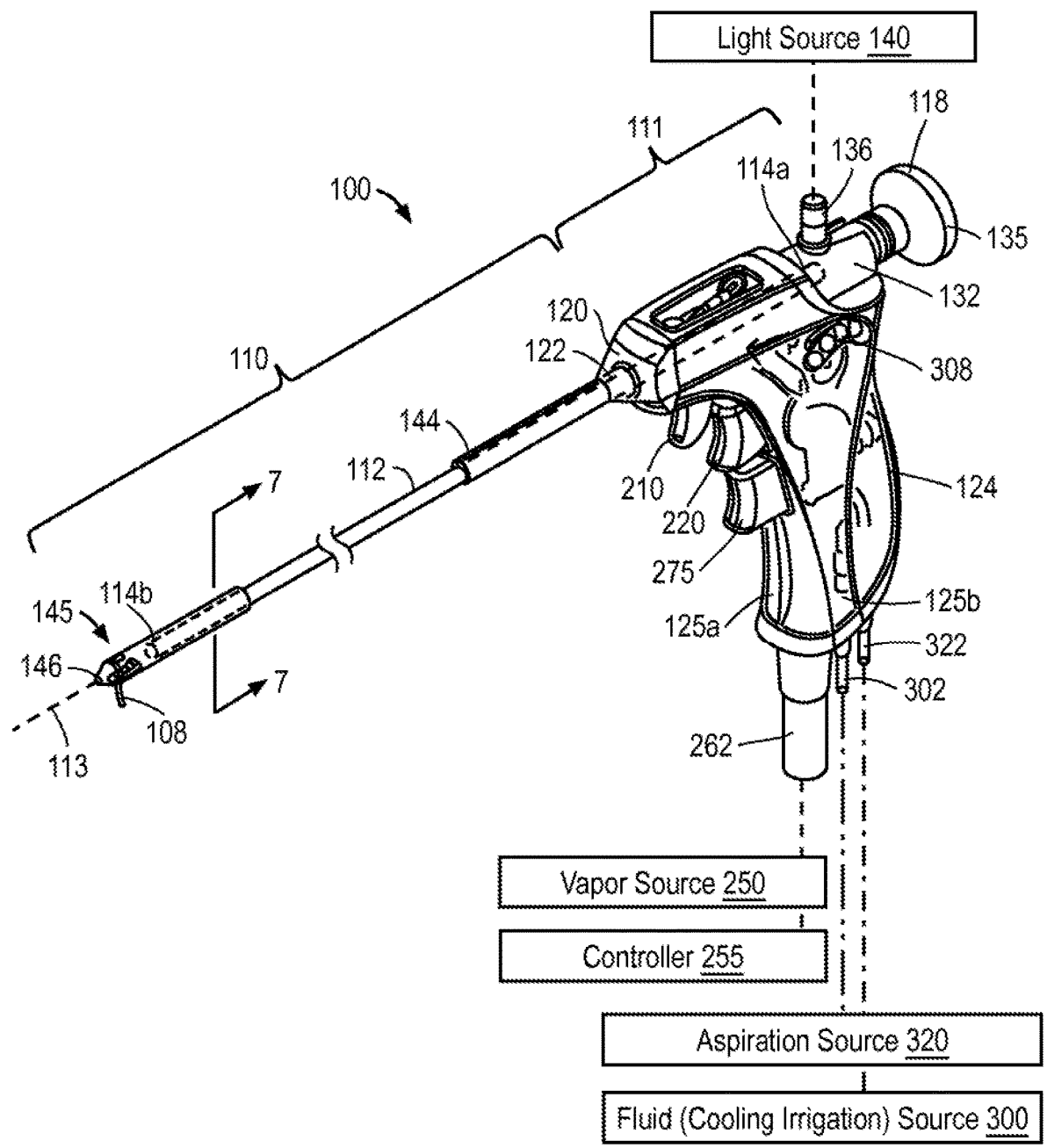
FIG. 4 is a perspective view of a probe corresponding to the invention.
Figure 5:
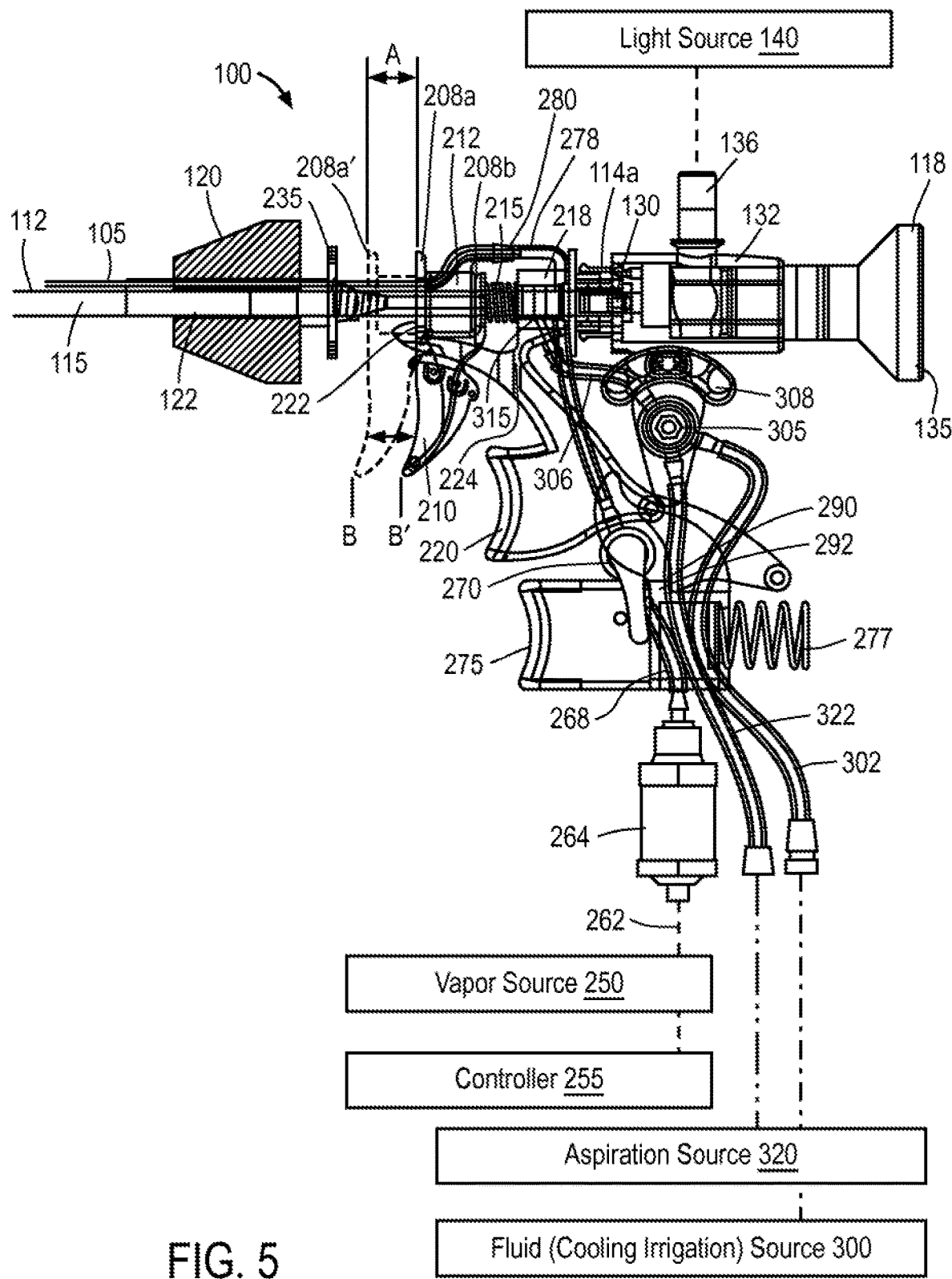
FIG. 5 is a view of components within a handle portion of the probe of FIG. 4.
Figure 6:
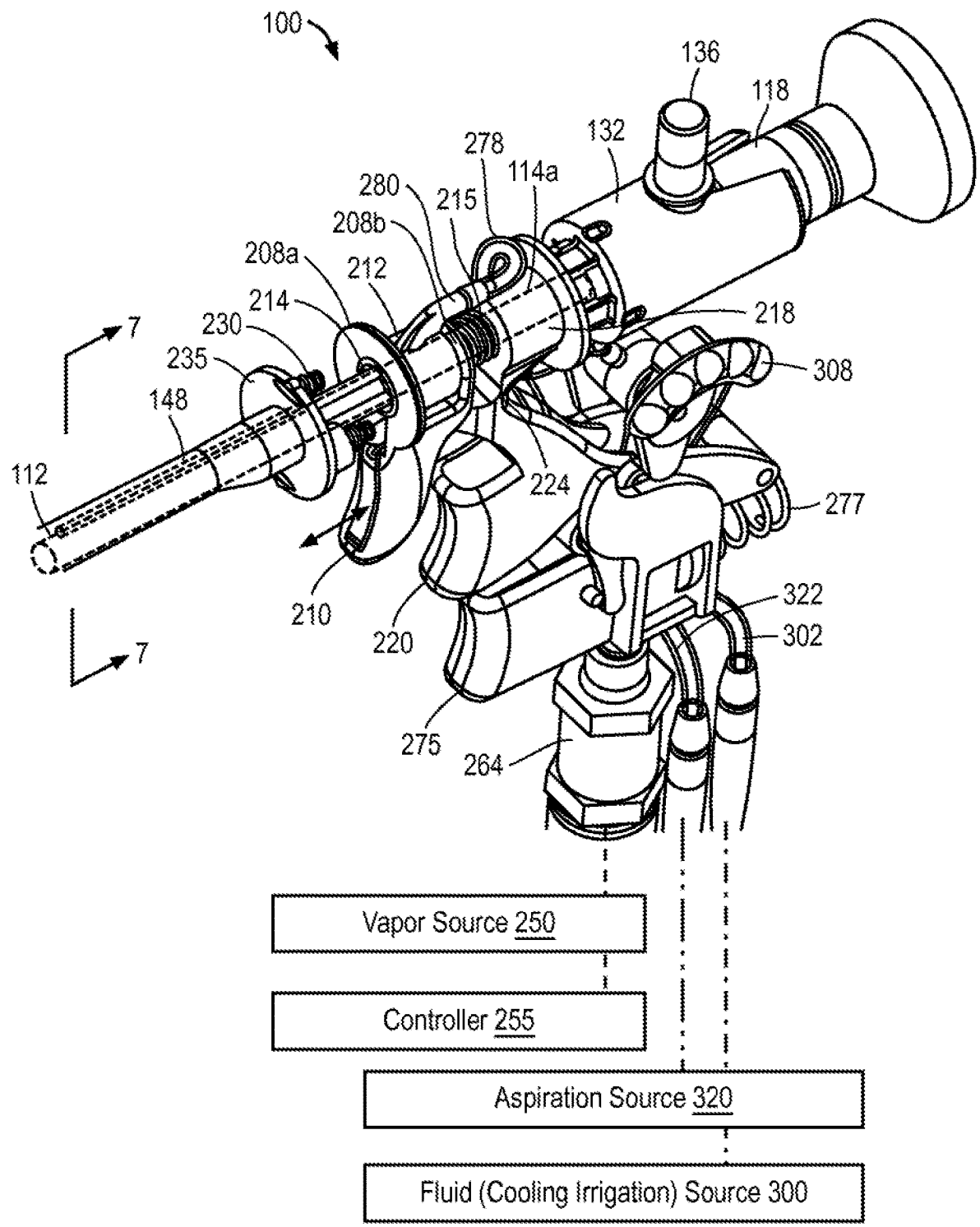
FIG. 6 is another view of components within a handle portion of the probe of FIG. 4.

FIGS. 4, 5 and 6 depict one embodiment of a probe 100 configured for trans-urethral access to the prostate which provides a viewing mechanism to view the urethra as the probe is navigated to a site in the interior of the patient's prostate. The probe 100 further carries an extendable and retractable microcatheter member 105 (FIG. 5) having a distal tip portion 108 (FIG. 4) configured to penetrate into precise targeted locations in transition zone tissue in prostate lobes to ablate targeted tissue volumes.

Handle and Introducer Portion

In FIG. 4, it can be seen that probe 100 has an elongate introducer portion 110 configured for insertion into the urethra and a handle portion 111 for gripping with a human hand. The key structural component of introducer portion 110 comprises a rigid introducer sleeve or extension sleeve 112 extending along longitudinal axis 113 with proximal end 114a and distal end 114b. A bore 115 (FIG. 5) in the rigid extension sleeve 112 extends along longitudinal axis 113. In one embodiment, referring to FIGS. 4 and 5, the extension sleeve 112 comprises a thin-wall stainless steel tube with bore 115 dimensioned to receive a commercially available viewing scope or endoscope 118. The schematic cut-away view of FIG. 5 shows structural bulkhead 120 coupled to a medial portion 122 of extension sleeve 112. The structure or bulkhead 120 comprises the structural member to which the molded handle having pistol grip 124, and more particularly the right- and left-side mating handle parts, 125a and 125b, are coupled (FIG. 4). The bulkhead can be a plastic molded part that can be fixed to sleeve 112 or rotationally coupled to sleeve 112.

Figure 7:
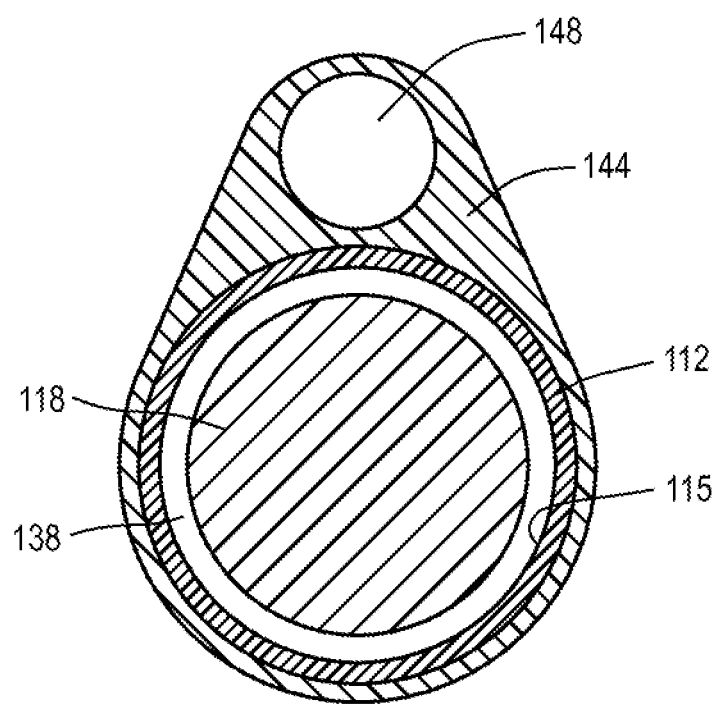
FIG. 7 is a sectional view of the extension portion of the probe of FIG. 4 taken along line 7-7 of FIGS. 4 and 6.

Referring to FIGS. 5-6, in which the molded handle left and right sides, 125a, 125b, are not shown, it can be seen that bore 115 in sleeve 112 has a proximal open end 130 into which the endoscope 118 can be inserted. The proximal end portion 114a of extension sleeve 112 can be coupled to an adapter mechanism 132 that releasably engages the endoscope 118 and rotationally aligns the endoscope 118 with the introducer portion 110. The endoscope 118 has a proximal viewing end 135 and light connector 136 extending outward from the viewing end 136 for coupling a light source 140 to the endoscope. FIG. 7 illustrates that bore 115 in sleeve 112 has a diameter ranging from about 2 to 5 mm for accommodating various endoscopes 118, while at the same time providing an annular space 138 for allowing an irrigation fluid to flow through bore 115 and outwardly from the introducer portion.

In one embodiment of probe 100, referring to FIGS. 5-8, the extendable-retractable microcatheter 105 comprises a thin-wall flexible polymer tube with a sharp tip that is axially slidable in a passageway 148 in the introducer portion 110. FIGS. 4, 7 and 9 show that the introducer portion 110 comprises an elongate introducer body 144 of plastic or another suitable material that surrounds extension sleeve 112. The introducer body 144 extends to a distal working end portion 145 having a blunt nose or tip 146 for advancing through the urethra. The elongate introducer body 144 is further configured with passageway 148 that accommodates the microcatheter member 105 as will be described below.

Figure 8:
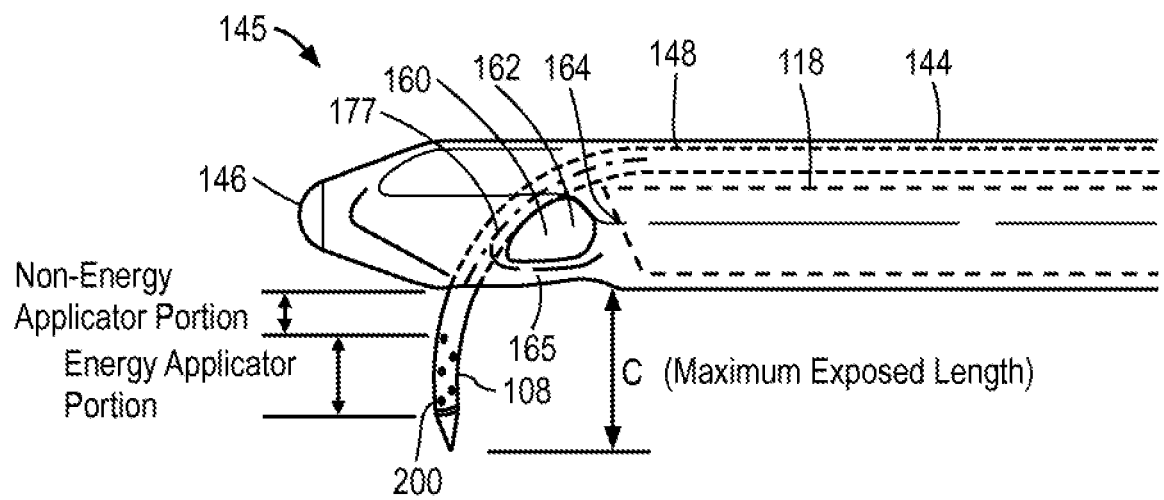
FIG. 8 is a side elevation view of the working end of the probe of FIG. 4 showing a flexible microcatheter or needle in an extended position extending laterally relative to the axis of the extension portion.
Figure 9:
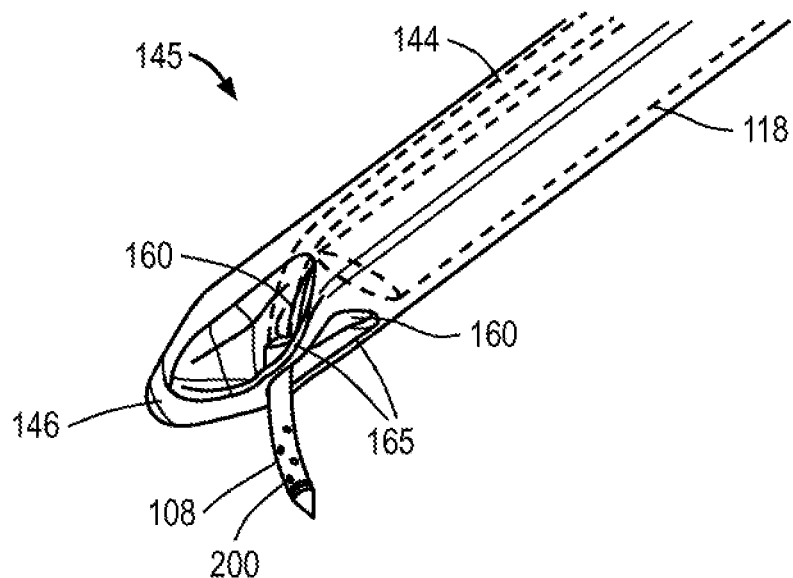
FIG. 9 is a perspective view of the working end of the probe of FIG. 4 showing the openings therein for viewing and the flexible microcatheter or needle in an extended position.

Referring to FIGS. 8-9, the distal end portion 145 of the introducer body 144 is configured with openings 160 that open to central open region 162 that is distal to the distal lens 164 of endoscope 118 that allows for viewing of the urethra through the lens 164 of the endoscope during navigation. The endoscope 118 can have a lens with a 30°, 12.5° or other angle for viewing through openings 160. As can be seen in FIGS. 8-9, the openings 160 have bridge elements 165 therebetween that function to prevent tissue from falling into central open region 162 of the introducer body 144. In FIG. 8, it can be seen that the working end portion 105 of the flexible microcatheter shaft 105 is disposed adjacent to open region 162 and thus can be viewed through the endoscope lens 164.

Microcatheter and Spring-Actuator

Figure 1:
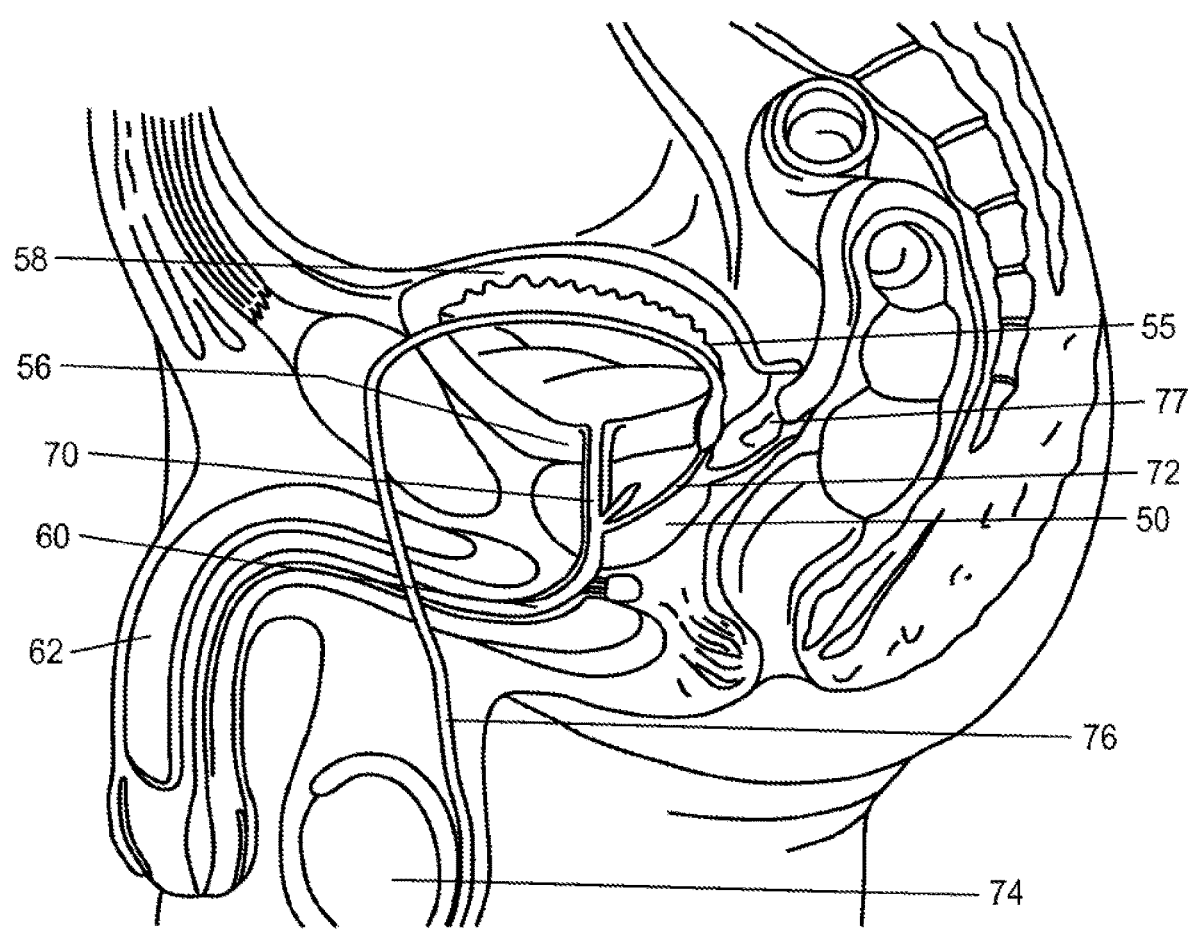
FIG. 1 is a sectional schematic view the male urogenital anatomy.
Figure 10:
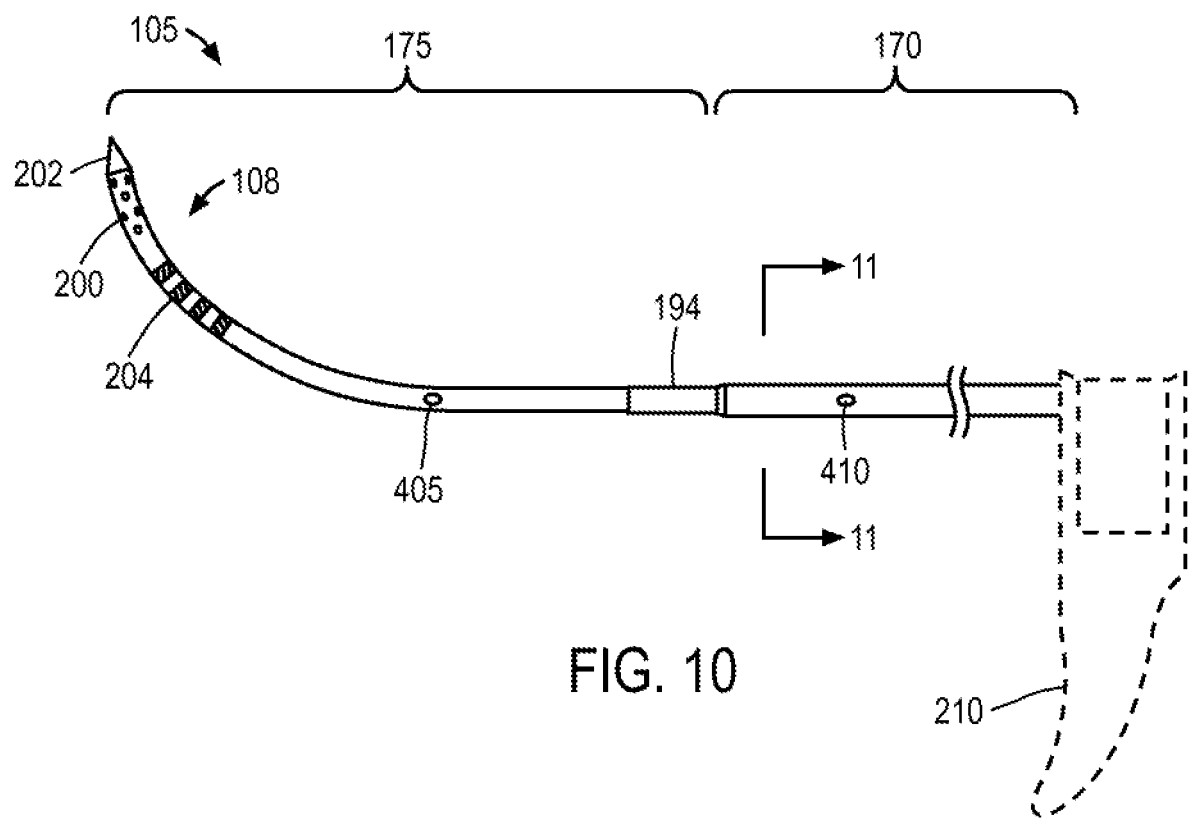
FIG. 10 is a side elevation view of the microcatheter or needle of the probe of FIG. 4 showing its dimensions and vapor outlets.
Figure 11:
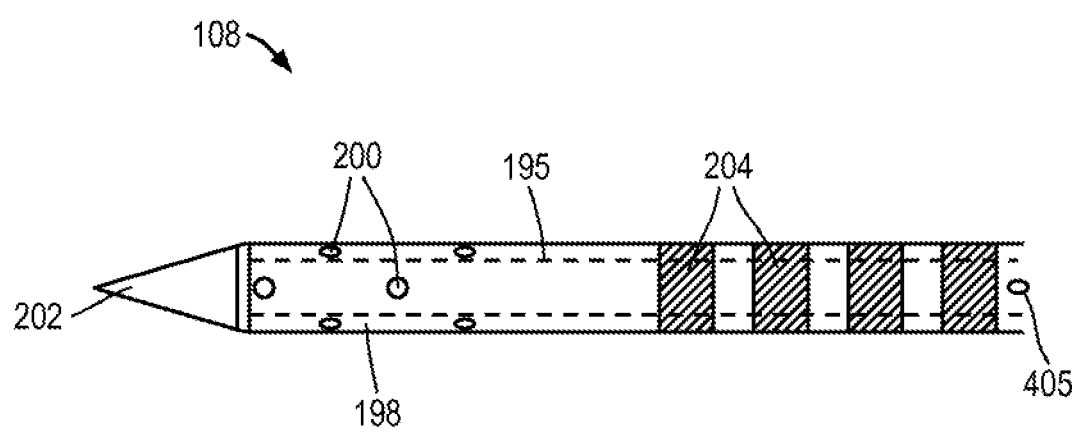
FIG. 11 is another view of a distal portion of the microcatheter of FIG. 10.
Figure 12:
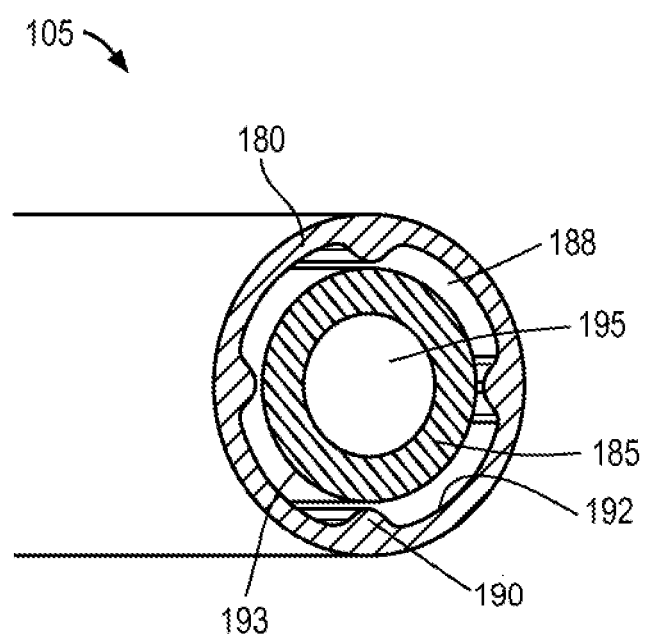
FIG. 12 is a sectional view of the microcatheter of FIG. 10 taken along line 11-11 of FIG. 10.

FIGS. 10-11 show the flexible microcatheter member or needle 105 de-mated from the probe 100 to indicate its repose shape. In one embodiment, the microcatheter 105 has a first (proximal) larger cross-section portion 170 that necks down to second (distal) cross-section portion 175 wherein the smaller second cross-section portion 175 has a curved repose shape with the curve configured to conform without significant resistance to the contour of the curved axis 177 of the path followed by the working end 108 of the microcatheter 105 as it is moved from its non-extended position to its extended position as shown in FIGS. 1, 8 and 9. In one embodiment, referring to FIGS. 10-12, the microcatheter's first cross section portion 170 comprises a thin wall outer sleeve 180 that is concentrically outward from inner microcatheter tube 185 that extends the length of the microcatheter member 105. As can be seen in FIG. 12, the outer sleeve 180 provides a thermally insulative air gap 188 around inner tubular member 185. In one embodiment shown depicted in FIG. 12, the outer sleeve 180 is configured with intermittent protrusions 190 that maintain the air gap 188 between the inner surface 192 of outer sleeve 180 and outer surface 193 of inner microcatheter tube. Referring back to FIG. 12, both the outer sleeve 180 and inner tubular member can comprise a high-temperature resistant polymer such as Ultem® that is suited for delivering a high temperature vapor as will be described below. In one embodiment, the microcatheter tube 185 has an outside diameter of 0.050" with an interior lumen 195 of approximately 0.030". Referring to FIG. 11, one embodiment of working end portion 108 for delivering vapor media to tissue has a thin wall 198 with a plurality of outlet ports 200 therein that are configured for emitting a condensable vapor media into tissue as will be described below. The outlet ports can range in number from about 2 to 100, and in one embodiment comprise of 12 outlets each having a diameter of 0.008" in six rows of two outlets with the rows staggered around the working end 108 as shown in FIGS. 10-11. In one embodiment shown in FIGS. 10-11, the distal-most tip 202 of the microcatheter 105 has a sharpened conical configuration that can be formed of a plastic material. As will be described below, it has been found that a polymeric needle and needle tip 202 is useful for its thermal characteristics in that its heat capacity will not impinge on vapor quality during vapor delivery.

FIGS. 10-11 further illustrate that the distal tip portion 108 of microcatheter 105 can have at least one marking 204 that contrasts with the color of the microcatheter 105 that is configured to be viewed through the endoscope (not shown). In one embodiment, the marking 204 can comprise annular marks of a first color that contrast with a second color of the microcatheter, wherein the marks are not visible through the endoscope when the microcatheter is in a retracted position. After the microcatheter is extended into tissue, the marks can be visible through the endoscope, which indicates that the microcatheter 105 has been extended into tissue.

Returning now to FIGS. 5 and 6, the cut-away view of the handle portion 111 shows the microcatheter member 105 and associated assemblies in the non-extended or retracted position. FIG. 5 shows flanges 208a and 208b of cocking actuator 210 are disposed on either side of actuator collar 212 that is coupled to proximal end 114a of the slidable microcatheter member 105. As can be understood from FIG. 5, the downward-extending cocking actuator 210 is adapted to cock the flanges 208a, 208b and microcatheter 105 to a cocked position which corresponds to the non-extended or retracted position of the microcatheter 105. In FIG. 5, the actuator 210 is shown in a first position B (phantom view) and second position B' following actuation with an index finger to thus cock the microcatheter member 105 to the second releasable non-extended position (or cocked position) B' from its extended position B. The flange 208a and actuator 210 is further shown in phantom view in the released position indicated at 208a'. In FIG. 5, the flanges 208a, 208b and associated assemblies are configured for an axial travel range indicated at A that can range from about 8 mm to 15 mm which corresponds to the travel of the microcatheter 105 and generally to the tissue-penetration depth. In the embodiment of FIG. 5, the flanges 208a, 208b and microcatheter member 105 are spring-actuatable to move from the non-extended position to the extended position by means of helical spring 215 disposed around sleeve 112. As can be seen in FIG. 5, the spring 215 is disposed between the slidable flange 208b and trigger block 218 that comprises a superior portion of the release trigger 220 which is configured to release the microcatheter 105 from its cocked position. In some embodiments, the release trigger 220 is configured to release the microcatheter 105 from its cocked or non-extended position into its extended position.

FIG. 5 further illustrates the release trigger 220 releasably maintaining the flange 205a and microcatheter 105 in its cocked position wherein tooth portion 222 of the trigger 220 engages the lower edge of flange 208a. It can be understood from FIG. 5 that the release trigger 220 is configured to flex or pivot around living hinge portion 224 when trigger 220 is depressed in the proximal direction by the physician's finger actuation. After actuation of trigger 220 and release of the microcatheter 105 to move distally, the axial travel of the assembly is configured to terminate softly rather than abruptly as flange 208a contacts at least one bumper element 230 as depicted in FIG. 6. The bumper elements 230 can comprise any spring or elastomeric element, and in FIG. 6 are shown as an elastomer element housed in a helical spring, which serve to cushion and dampen the end of the travel of the spring-driven microcatheter assembly. The bumper elements 230 are coupled to flange 235 which in turn is configured to be fixed between right- and left-side handle parts 125a and 125b (FIG. 4).

Now turning to the energy-delivery aspect of the system, a vapor source 250 is provided for delivering a vapor media through the microcatheter member 105 to ablate tissue. The vapor source can be a vapor generator that can deliver a vapor media, such as water vapor, that has a precisely controlled quality to provide a precise amount of thermal energy delivery, for example measured in calories per second. Descriptions of suitable vapor generators can be found in the following U.S. application Ser. Nos. 11/329,381; 12/167,155; 12/389,808; 61/068,049; 61/068,130; 61/123,384; 61/123,412; 61/126,651; 61/126,612; 61/126,636; 61/126,620 all of which are incorporated herein by reference in their entirety. The vapor generation system also can comprise an inductive heating system similar to that described in U.S. Application Nos. 61/123,416, 61/123,417, and 61/126,647. The system further includes a controller 255 that can be set to control the various parameters of vapor delivery, for example, the controller can be set to deliver vapor media for a selected treatment interval, a selected pressure, or selected vapor quality.

Referring to FIGS. 4-5, in one embodiment, the vapor source 250 can be remote from the handle 124 and vapor media is carried to the handle by a flexible conduit 262 that couples handle and check valve 264 therein. In one embodiment, vapor can be re-circulated in conduit 262 until a solenoid in the vapor source is actuated to cause the vapor flow to thus provide an increased fluid pressure which opens the check valve 264 and allows the vapor media to flow through flexible tube 268 to valve 270 that can be finger-actuated by trigger 275. In one embodiment depicted in FIG. 5, the trigger 275 is urged toward a non-depressed position by spring 277 which corresponds to a closed position of valve 270. The trigger 275 also can be coupled by an electrical lead (not shown) to controller 255. Thus, actuating the trigger 275 can cause the controller to actuate a solenoid valve in the vapor generator to cause vapor flow through the relief valve. As a safety mechanism, the valve 270 in the handle is opened only by its actuation to thus permit the flow of vapor media through flexible tube 278 which communicates with inflow port portion 280 of collar 212 which in turn communicates with the lumen 195 (FIG. 12) in the microcatheter 105. Thus, FIG. 5 illustrates the flow path and actuation mechanisms that provide vapor flow on demand from the vapor source 250 to the vapor outlets 200 in working end 108 of the microcatheter 105.

As can be seen in FIG. 5, the handle can also provide an interlock mechanism that prevents the actuation of vapor flow if the microcatheter release trigger is in the cocked position, wherein edge portion 290 coupled to release trigger 220 can engage notch 292 in trigger 275 to prevent depression of said trigger 275.

Still referring to FIG. 5, one embodiment of the system includes a fluid irrigation source 300 that is operatively couple to the bore 115 in extension member 112 to deliver a fluid outward from the bore 115 to the open region 162 of the probe working end 145 (see FIG. 8). As can be seen in FIG. 7, the bore 115 is dimensioned to provide a space 138 for fluid irrigation flow around the endoscope 118. In FIG. 5, it can be seen that fluid source 300, which can be a drip bag or controlled pressure source of saline or another fluid, is detachably coupled to tubing 302 in the handle which extends to a valve 305 that can be thumb-operated from actuators 308 on either side of the handle. The thumb actuator 308 can also control the rate of flow of the irrigation fluid by moving the actuator 308 progressively forward, for example, to open the valve more widely open. The fluid flows from valve 305 through tube 306 to a port or opening 315 in the extension sleeve 112 to thus enter the bore 115 of the sleeve.

FIG. 5 further depicts an aspiration source 320 operatively coupled to tubing 322 in the handle 124 which also can be actuated by valve 305 wherein the thumb actuator 308 can be rocked backwardly to allow suction forces to be applied through the valve 305 to tubing 306 that extends to port 315 in the extension member—which is the same pathway of irrigation flows. Thus, suction or aspiration forces can withdraw fluid from the working end of the device during a treatment.

In another aspect of the invention, referring to FIGS. 10-11, the microcatheter 105 carries a temperature sensor or thermocouple 405 at a distal location therein, for example as indicated in FIG. 10. The thermocouple is operatively connected to controller 255 to control vapor delivery. In one embodiment, an algorithm reads an output signal from the thermocouple 405 after initiation of vapor delivery by actuation of trigger 275, and in normal operation the thermocouple will indicate an instant rise in temperature due to the flow of vapor. In the event, the algorithm and thermocouple 405 do not indicate a typical rise in temperature upon actuation of trigger 275, then the algorithm can terminate energy delivery as it reflects a system fault that has prevented energy delivery.

In another embodiment, referring again to FIGS. 10-11, the microcatheter 105 can carry another temperature sensor or thermocouple 410 in a portion of microcatheter 105 that resides in passageway 148 of the introducer body 144. This thermocouple 410 is also operatively connected to controller 255 and vapor source 250. In one embodiment, an algorithm reads an output signal from thermocouple 410 after initiation of vapor delivery and actuation of actuator 308 that delivers an irrigation fluid from source 300 to the working end 145 of the probe. The delivery of irrigation fluid will maintain the temperature in the region of the thermocouple at a predetermined peak level which will not ablate tissue over a treatment interval, for example below 55° C., below 50° C. or below 45° C. If the temperature exceeds the predetermined peak level, the algorithm and controller can terminate vapor energy delivery. In another embodiment, a controller algorithm can modulate the rate of cooling fluid inflows based on the sensed temperature, and/or modulate the vapor flow in response to the sensed temperature. In an alternative embodiment, the thermocouple 410 can be in carried in a portion of introducer body 144 exposed to passageway 148 in which the microcatheter resides.

Method of Use

Figure 13A:
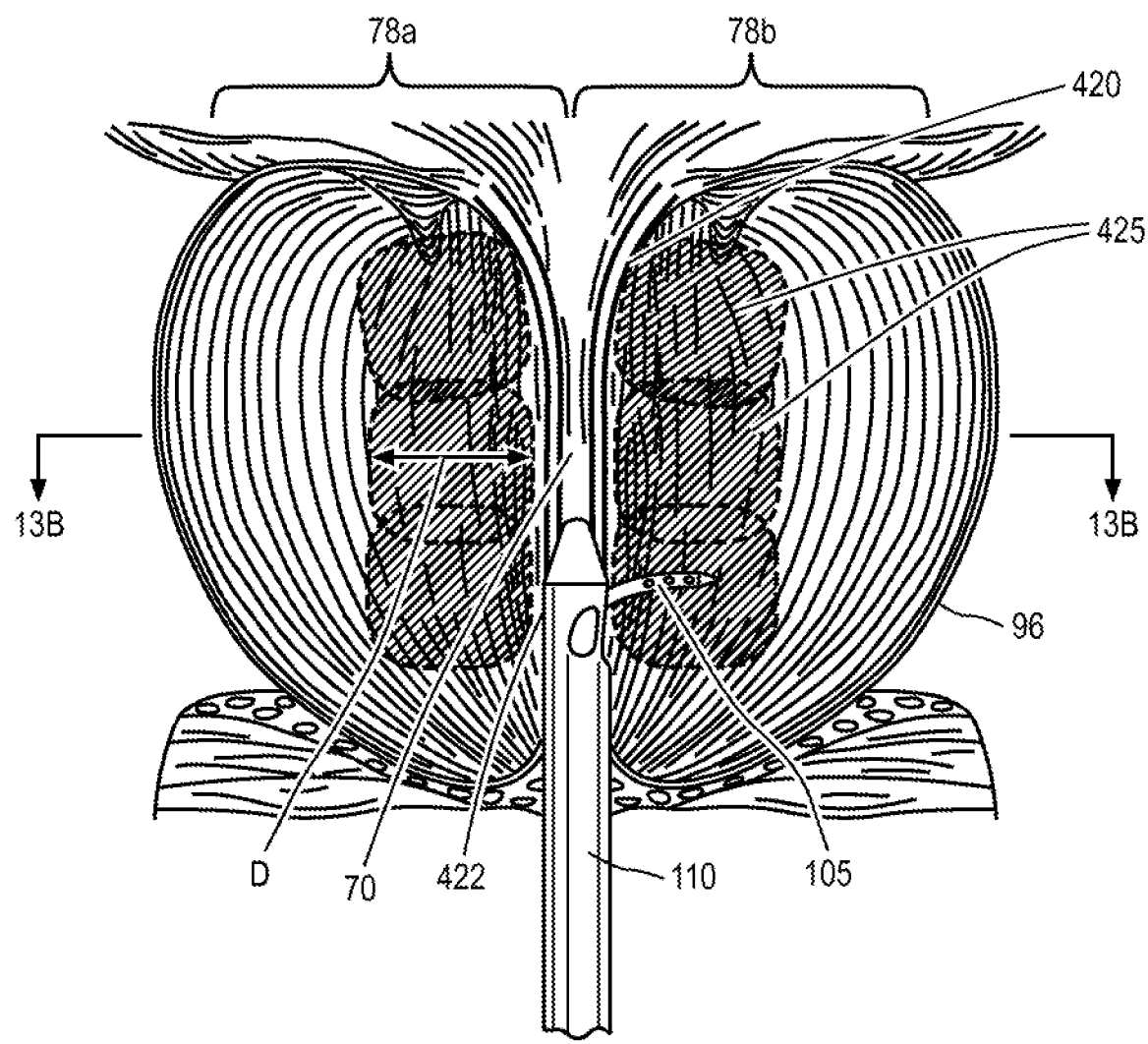
FIG. 13A is a longitudinal sectional schematic view of a prostate showing a method of the invention in treating transition zone tissue adjacent the prostatic urethra.
Figure 13B:
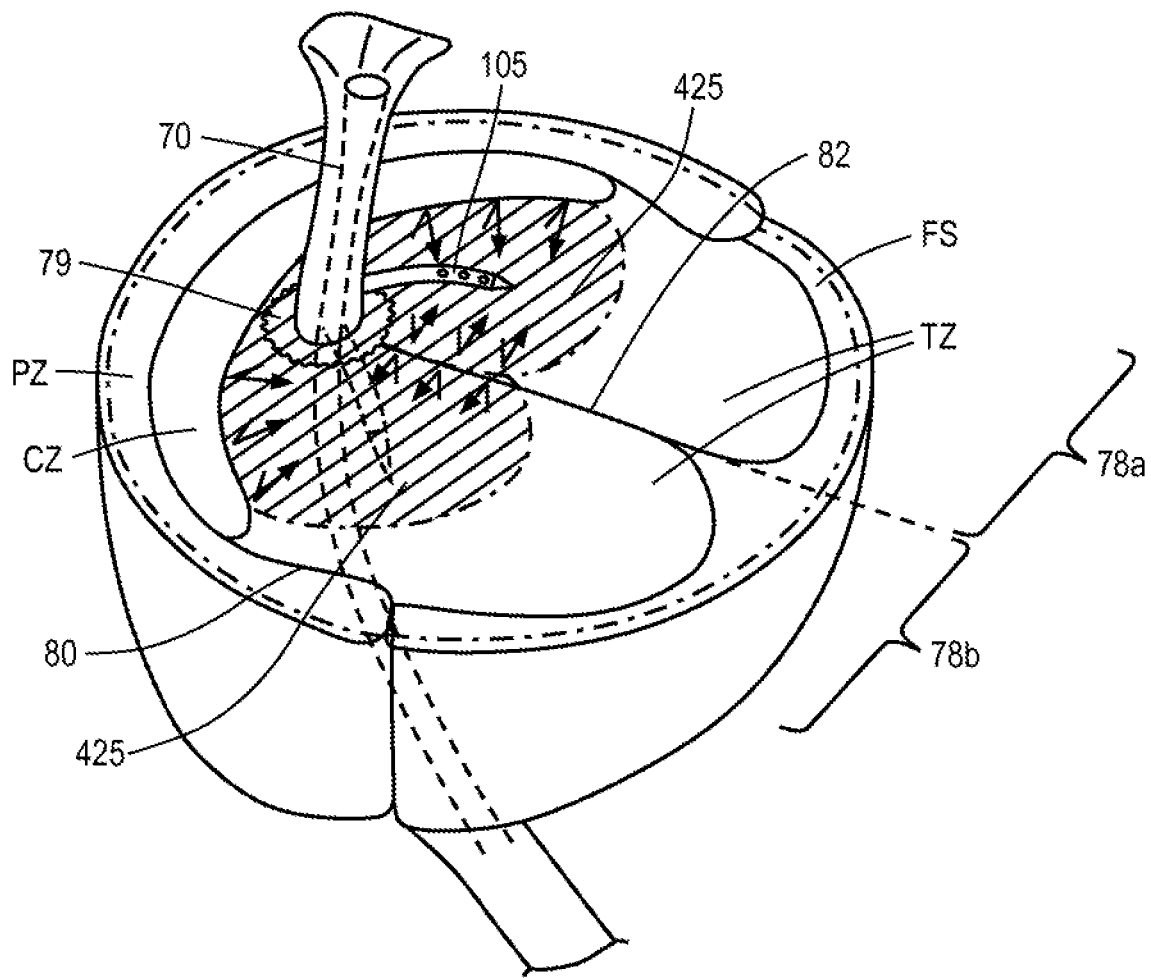
FIG. 13B is a transverse sectional view of the prostate of FIG. 13A taken along line 13B-13B of FIG. 13A illustrating the containment of the ablation in transition zone tissue adjacent the prostatic urethra.

Referring to FIGS. 13A and 13B, the device and method of this invention provide a precise, controlled thermal ablative treatment of tissue in first and second lateral prostate lobes, 78a and 78b. Additionally, the device of the invention can be used to treat an affected median lobe in patients with an enlarged median lobe. In particular, the ablative treatment is configured to ablate smooth muscle tissue, to ablate alpha adrenergic (muscle constriction) receptors, and to ablate sympathetic nerve structures. More in particular, the method of ablative treatment is configured to target such smooth muscle tissue, alpha adrenergic receptors, and sympathetic nerve structures parallel to the prostatic urethra in transition zone tissue TZ between the bladder neck region 420 and the verumontanum region 422 as depicted in FIGS. 13A-13B. The targeted ablation regions 425 can have a depth indicated at D in FIGS. 13A-13B that is less than 2 cm outward from the prostatic urethra 70, or less than 1.5 cm outward from the urethra. In another embodiment, the targeted ablation regions can have a depth D that is less than 12 mm outward from the prostatic urethra 70. In one embodiment, the targeted ablation region has a depth D between 10 mm-12 mm from the prostatic urethra. Depending on the length of the patient's prostatic urethra 70, the number of energy deliveries and ablated regions 425 can range from 2 to 4 and typically is 2 or 3.

In a method of use, the physician can first prepare the patient for trans-urethral insertion of the extension portion 110 of probe 100. In one example, the patient can be administered orally or sublingually a mild sedative such as Valium, Lorazepam or the like from 15 to 60 minutes before the procedure. Of particular interest, it has been found that prostate blocks (injections) or other forms of anesthesia are not required due to lack of pain associated with an injection of a condensable vapor. The physician then can actuate the needle-retraction actuator 210, for example with an index finger, to retract and cock the microcatheter 105 by axial movement of the actuator (see FIGS. 4-6). By viewing the handle 124, the physician can observe that the microcatheter 105 is cocked by the axial location of trigger 210. A safety lock mechanism (not shown) can be provided to lock the microcatheter 105 in the cocked position.

Next, the physician can advance the extension portion 110 of the probe 100 trans-urethrally while viewing the probe insertion on a viewing monitor coupled to endoscope 118. After navigating beyond the verumontanum 422 to the bladder neck 420 (FIG. 13A), the physician will be oriented to the anatomical landmarks. The landmarks and length of the prostatic urethra can be considered relative to a pre-operative plan based on earlier diagnostic ultrasound images or other images, such as MRI images.

Figure 14:
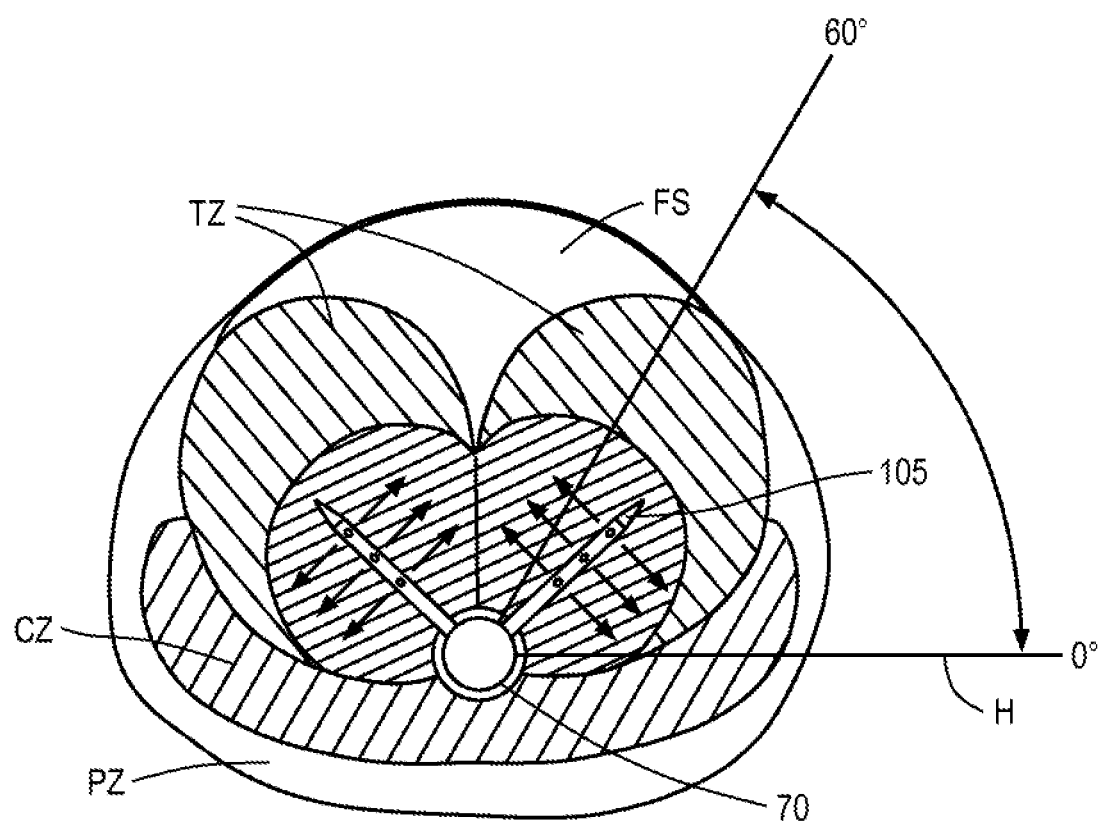
FIG. 14 is a transverse sectional view of a prostate showing the range or radial angles in which the microcatheter of the invention in introduced into transition zone tissue.

As can be seen in FIG. 14, the physician can rotate the handle of the probe relative to the horizontal plane H from 0° to about 60° upwardly, to insure that the microcatheter 105 penetrates into a central region of the transition zone tissue TZ (see FIGS. 13B and 14). After the physician rotates the microcatheter-carrying probe about its axis to orient the microcatheter within the range of angles depicted in FIG. 14, the release trigger 220 can be actuated to thereby penetrate the microcatheter 105 into the prostate lobe. Thereafter, the vapor actuation trigger 275 can be actuated to deliver vapor media into the prostate tissue for a treatment interval of approximately 30 seconds or less, or 20 seconds or less. In one embodiment, the vapor delivery interval is 10 seconds.

FIG. 13A depicts a complete treatment which includes cocking the microcatheter 105, re-positioning the microcatheter, and releasing the microcatheter followed by vapor delivery in a plurality of locations in each lobe, for example for a total of three vapor injections in each lobe (i.e., for a total of six "sticks" of the microcatheter into the prostate). The schematic view of FIG. 13A thus illustrates a method the invention wherein three penetrations of microcatheter 105 are made sequentially in a prostate lobe and the treatment interval, the vapor pressure and calories/sec provided by vapor energy are selected to produce slightly overlapping ablations or lesions to ablate the smooth muscle tissue, alpha adrenergic receptors, and sympathetic nerve structures in a region parallel to the prostatic urethra. The pressure of the vapor media exiting the vapor outlets 200 can be between 40 mmHg and 50 mmHg. The system can deliver a vapor media configured to provide energy in the range of 1 to 40 cal/sec at pressures at the tissue interface ranging from about 20 mmHg to 200 mmHg. The system can utilize a source of vapor media that provides a vapor having a temperature of at least 60° C., 80° C., 100° C., 120° C., or 140° C. The method of the invention, when compared to the prior art, can reduce the total volume burden of ablated tissue and thus can lessen the overall inflammatory response. This aspect of the method can lead to more rapid tissue resorption, more rapid clinical improvement and can eliminate the need for post-treatment catheterization.

In another embodiment, the urethra can be irrigated with a cooling fluid from source 300 (see FIGS. 5-6) throughout the selected interval of energy delivery. It has been found that such a flow of cooling fluid may be useful, and most important the flow of cooling fluid can be continuous for the duration of the treatment interval since such times are short, for example 10 to 30 seconds at each treatment location. Such a continuous flow method cannot be used in prior art methods, such as RF ablation methods, since the cooling fluid volume accumulates in the patient's bladder and the lengthy RF treatment intervals would result in the bladder being filled rapidly, resulting in further time-consuming steps to withdraw the RF probe, removing the excess irrigation fluid volume and then re-starting the treatment.

Figure 15:
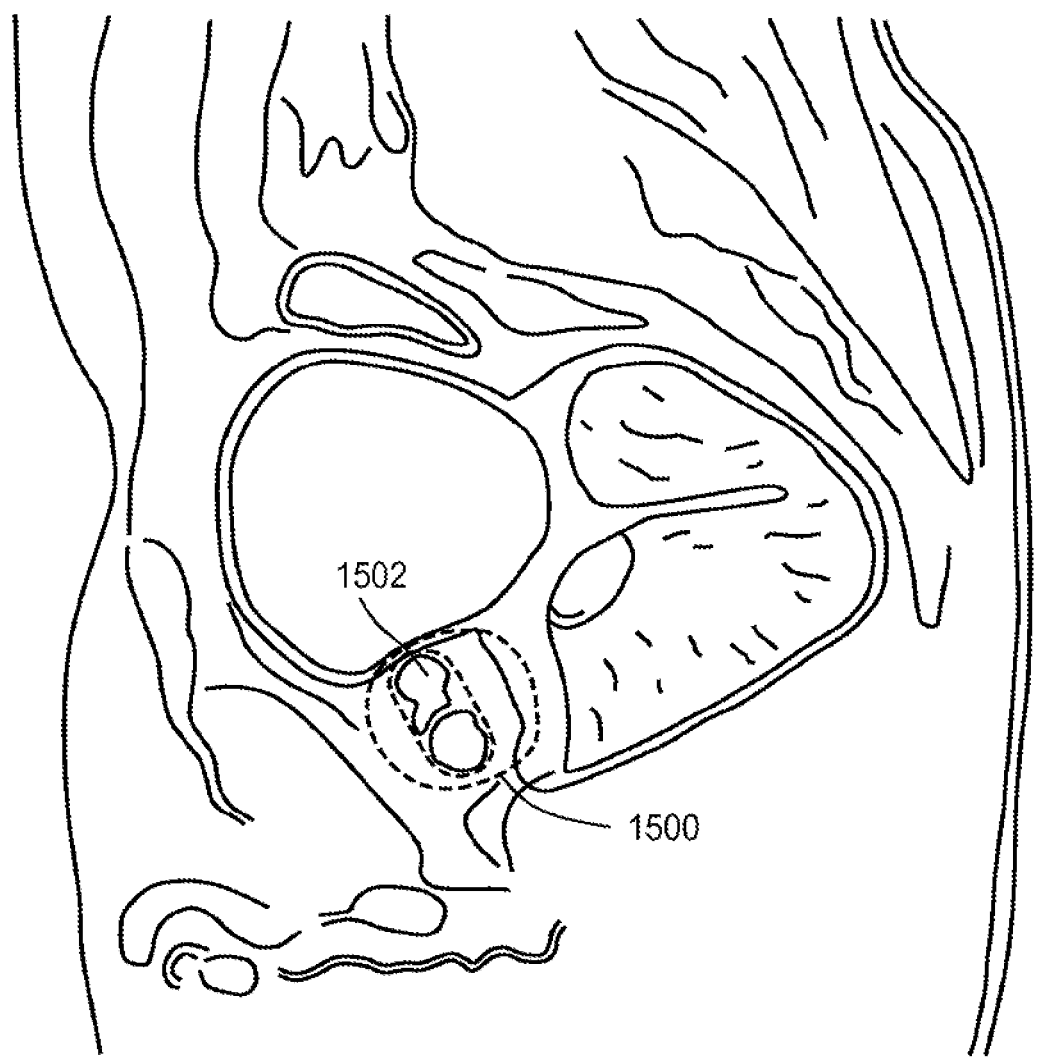
FIG. 15 is an MRI of a BPH patient 1 week after a treatment as indicated schematically in FIGS. 13A-13B.

FIG. 15 is a sagittal MRI image of an exemplary treatment of a BPH patient 1 week following the procedure, in which the treatment included the following steps and energy delivery parameters. The patient's prostate weighed 44.3 gms based on ultrasound diagnosis. Amparax (Lorazepam) was administered to the patient 30 minutes before the procedure. In the treatment of the patient in FIG. 15, each treatment interval comprised of 10 seconds of vapor delivery at each of six locations in transition zone TZ tissue (3 injections in each lobe). Thus, the total duration of actual energy delivery was 60 seconds in the right and left prostate lobes. The energy delivered was 5 cal/sec, or 50 calories per treatment location 425 (FIG. 13A) and a total of 300 total calories delivered to create the targeted ablation parallel to the prostatic urethra 70, which can be seen in the MRI of FIG. 15. The vapor media comprised water vapor having a temperature of approximately 100° C.

By comparing the method of the present invention of FIGS. 13A-13B with prior art methods, it can be understood the present invention is substantially different than the prior art. Prior art RF needles typically are elongated, which ablates tissue away from the prostatic urethra and does not target tissue close to and parallel to the prostatic urethra. Second, many prior art RF energy delivery methods apply RF energy for 1 to 3 minutes or longer which allows thermal diffusion to reach the capsule periphery, unlike the very short treatment intervals of the method of the present invention which greatly limit thermal diffusion. Third, most prior art RF energy delivery methods do not create a uniform ablation of tissue adjacent and parallel to the prostatic urethra to ablate smooth muscle tissue, alpha adrenergic receptors, and sympathetic nerve structures in a region parallel to the prostatic urethra.

In another embodiment of the method of the invention, referring again to FIG. 13B, the vapor delivery member or microcatheter 105 is introduced into selected locations in the transition zones tissue TZ as described above. The transition zone tissue TZ comprises the region in which substantially all benign hyperplastic growth occurs, and therefore this tissue impinges on the urethra resulting in symptoms of BPH. In a method of the invention, the selected radial angle of the microcatheter as show in FIG. 14 thus provides injection of the vapor media into a central portion of such transition zone tissue TZ which allows for ablation of transition zone tissue without ablating non-transition zone tissue. This aspect of the method is enabled by the use of vapor media, a form of convective heating, and wherein such convective heating does not propagate beyond denser tissue or fibrous layers that surround the transition zone tissue TZ. Thus, energy delivered from condensation of the vapor media will be confined to the treated region of the transition zone tissue TZ, since vapor propagation is impeded by tissue density. FIG. 13B depicts that the propagation of vapor media is reflected from tissues that interface with transition zone tissue TZ, which tissue includes the prostatic urethra 70, central zone tissue, a fibrous layer or plane 92 between the lobes 78a, 72b, a fibrous layer 80 adjacent peripheral zone tissue PZ, and the fibromuscular stroma FS. The method of ablation is advantageous in that only the tissue causally related to BPH is ablated and thereafter resorbed. In prior art methods that utilize RF energy, the applied energy can cross natural boundaries between tissue zones since RF current flow and resultant Joule heating is only influenced by electrical impedance, and not by tissue density. The additional advantage is that the ablated tissue burden can be significantly reduced, when compared to other modalities of energy delivery, such as RF. The reduced burden of ablated tissue in turn lessens the overall inflammatory response, and will lead to more rapid patient recovery.

In another aspect of the invention, referring to FIG. 13A, the vapor media propagation and convective heating can extend adjacent a selected length of the prostatic urethra 70 from the bladder neck 420 to verumontanum 422 within the transition zone tissue TZ, while leaving prostatic urethra undamaged which in turn can eliminate the need for post-treatment catheterization. In another aspect of the invention, the vapor propagation, when confined to transitional zone tissue TZ, further ensures that no unwanted tissue heating or ablation will occur outward of the prostatic capsule 96 where nerves and nerve bundles are located. The treated tissue geometry within transition zone tissue TZ can be limited to region adjacent the prostatic urethra 70 without damage to prostate tissue outward from the urethra greater than 1.5 cm or greater that 2.0 cm.

Figure 16:
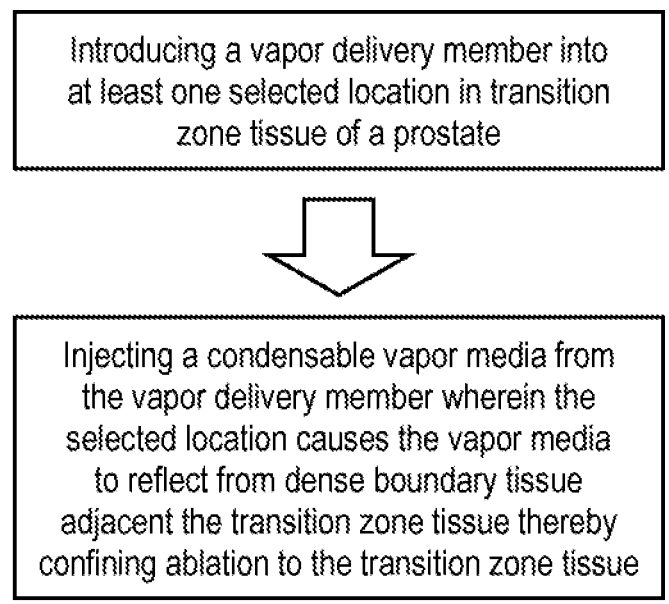
FIG. 16 is a block diagram of a method corresponding to the invention.

One method corresponding to the invention is shown in the block diagram of FIG. 16, which includes the steps of advancing a probe trans-urethrally to the patient's prostate, introducing a vapor delivery member into at least one selected location in transition zone TZ tissue of a prostate, and injecting a condensable vapor media from the vapor delivery member wherein the selected location causes the vapor media to reflect from boundary tissue adjacent the transition zone tissue to thereby confine vapor condensation and heating to the transition zone tissue. In general, a method for treating BPH comprises introducing a vapor delivery member into prostatic transition zone tissue, and injecting vapor media into a selected location that is at least partly surrounded by another outward tissue with a higher density, wherein the outward tissue either reflects propagation of the vapor media or has a build-up of interstitial pressure therein (due to vapor media injection) which impeded the flow of vapor outwardly to thereby confine the vapor-induced thermal treatment to the targeted transition zone tissue.

Figure 17:
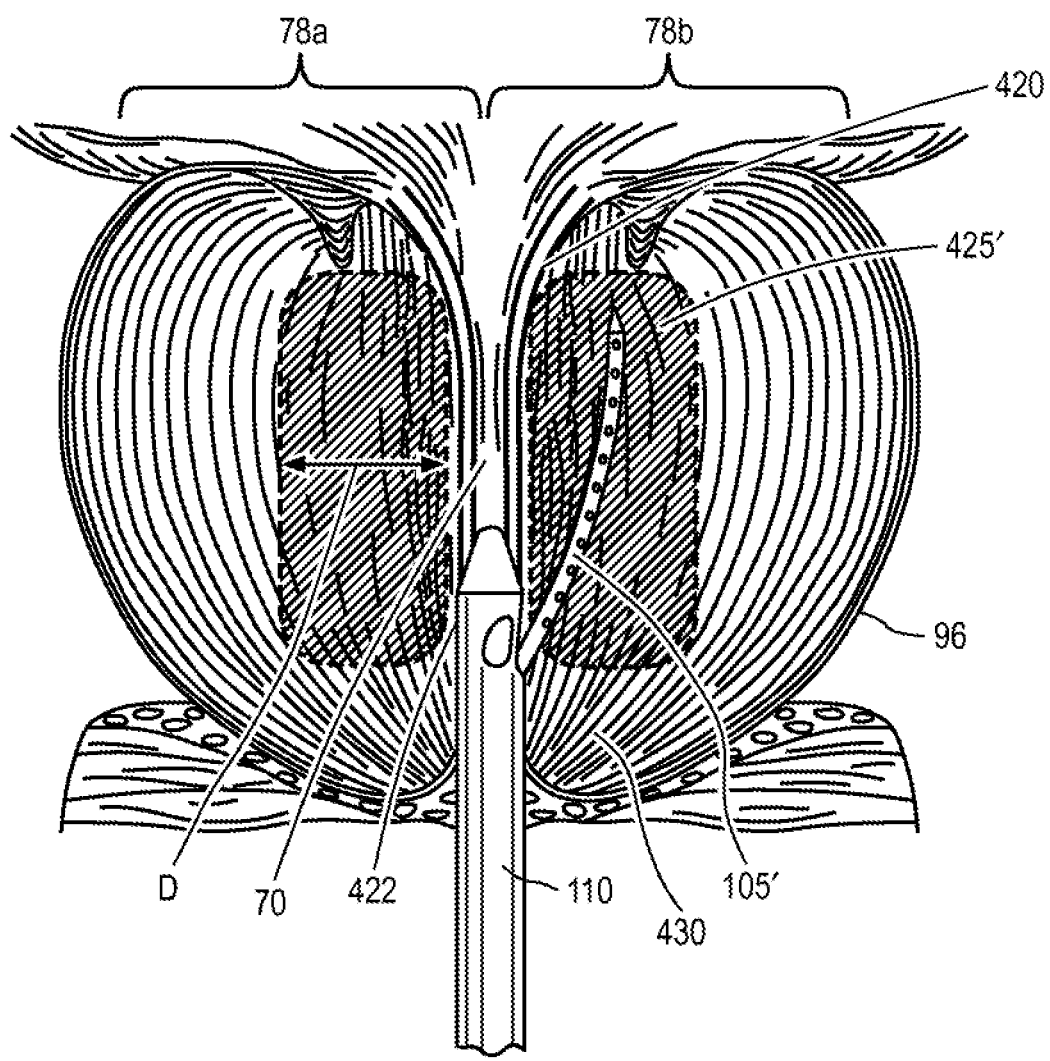
FIG. 17 is a longitudinal sectional schematic view of a prostate showing a method of treating transition zone tissue with an elongated needle introduced parallel to the prostatic urethra.

In another aspect of the invention, referring to FIG. 17, a similar method for treating BPH comprises introducing a vapor delivery needle 105' into transition zone tissue TZ from a location near the apex 430 of the prostate, advancing the working end of needle 105' end substantially parallel to the prostatic urethra 70, and introducing vapor from the working end to ablate a region of the transition zone tissue adjacent the urethra similar to the treatment of FIGS. 13A-13B. An apparatus and method utilizing such an elongate needle was disclosed in co-pending U.S. patent application Ser. No. 12/614,218. It should be appreciated that a vapor delivery needle also can be introduced into the targeted transition zone tissue from a trans-rectal approach and viewed under ultrasound as disclosed in U.S. patent application Ser. No. 12/687,734.

In another embodiment, the system include a vapor delivery mechanism that delivers controlled and substantially predetermined amount of energy, and thus controlled amount of energy, over a variable time interval wherein injection pressure varies in response to tissue characteristics.

As for additional details pertinent to the present invention, materials and manufacturing techniques may be employed as within the level of those with skill in the relevant art. The same may hold true with respect to method-based aspects of the invention in terms of additional acts commonly or logically employed. Also, it is contemplated that any optional feature of the inventive variations described may be set forth and claimed independently, or in combination with any one or more of the features described herein. Likewise, reference to a singular item, includes the possibility that there are plural of the same items present. More specifically, as used herein and in the appended claims, the singular forms "a," "and," "said," and "the" include plural referents unless the context clearly dictates otherwise. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation. Unless defined otherwise herein, all technical and scientific terms used herein have the same meaning as commonly understood by one of ordinary skill in the art to which this invention belongs. The breadth of the present invention is not to be limited by the subject specification, but rather only by the plain meaning of the claim terms employed.

What is claimed is:

1. A medical device, comprising:
   a handle portion configured to be gripped by a hand of an operator;
   an introducer portion extending from a proximal end toward a distal tip and configured to be inserted into a urethra of a patient, wherein the introducer portion defines:
      a first lumen,
      a second lumen configured to receive an imaging device,
      a gap distal to a distalmost end of the second lumen, wherein a distal tip of the introducer portion is distal to the gap; and
      a bridge extending across the gap to define at least two openings that are each in communication with (a) the gap and (b) a distal opening of the first lumen; and
   a needle disposed in the first lumen, wherein the needle defines a channel configured to be in fluid communication with a source of vapor, and wherein a distal portion of the needle includes at least one outlet in fluid communication with the channel;
   wherein the medical device is configured to be transitioned from a first configuration to a second configuration, wherein, in the first configuration, the distal portion of the needle is within the first lumen, and wherein, in the second configuration, the distal portion of the needle extends out of a distal opening of the first lumen, through the gap, and through one of the at least two openings, such that the distal portion of the needle is transverse to a longitudinal axis of the introducer portion.

2. The medical device of claim 1, wherein the distal tip is blunt.

3. The medical device of claim 1, wherein the distal portion of the needle includes a marking extending around a circumference of the needle.

4. The medical device of claim 1, wherein a cross-section of the introducer portion perpendicular to the longitudinal axis of the introducer portion, and including the first lumen and the second lumen, includes a first curved portion and a second curved portion, and wherein the first curved portion has a different radius of curvature than the second curved portion.

5. The medical device of claim 4, wherein the cross-section further includes first and second straight sides extending between the first curved portion and the second curved portion.

6. The medical device of claim 1, wherein the longitudinal axis of the introducer portion passes through the second lumen, the gap, and the distal tip, and wherein, in the second configuration, the longitudinal axis of the introducer portion intersects the needle.

7. The medical device of claim 1, wherein a width of the bridge is narrower than a width of each of the at least two openings.

8. A medical device, comprising:
   an introducer portion extending from a proximal end toward a distal tip and configured to be inserted into a urethra of a patient, wherein the introducer portion defines a first lumen extending along a first longitudinal axis of the introducer portion and a second lumen extending along a second longitudinal axis of the introducer portion, and wherein the second lumen is configured to receive an imaging device; and
   a needle received in the first lumen, wherein the needle defines a channel, and wherein a distal portion of the needle defines an outlet in fluid communication with the channel;
   wherein a radial outer surface of the introducer portion defines a radial opening distal to a distalmost end of the second lumen, and
   wherein the medical device is configured to be transitioned from a first configuration to a second configuration, wherein, in the first configuration, the distal portion of the needle is within the first lumen, wherein, in the second configuration, the distal portion of the needle extends out of a distal opening of the first lumen and through the radial opening, and wherein, in the second configuration, the second longitudinal axis intersects the needle, wherein a bridge longitudinally spans a gap in communication with the radial opening and the distal opening of the first lumen.

9. The medical device of claim 8, wherein the distal portion of the needle includes a marking extending around a circumference of the needle.

10. The medical device of claim 8, wherein a cross-section of the introducer portion perpendicular to the second longitudinal axis, and including the first lumen and the second lumen, includes a first curved portion and a second curved portion, and wherein the first curved portion has a different radius of curvature than the second curved portion.

11. The medical device of claim 10, wherein the cross-section further includes first and second straight sides extending between the first curved portion and the second curved portion.

12. The medical device of claim 8, wherein the distal tip of the introducer portion is distal to the gap, and wherein the second longitudinal axis passes through the gap.

13. The medical device of claim 8, wherein the gap is in fluid communication with the radial opening and the distal opening of the first lumen.

14. A medical device, comprising:
an introducer portion extending from a proximal end toward a distal tip and configured to be inserted into a urethra of a patient, wherein the introducer portion defines a first lumen extending along a first longitudinal axis of the introducer portion, and a second lumen extending along a second longitudinal axis of the introducer portion, wherein the second lumen is configured to receive an imaging device; and
a needle received in the first lumen, wherein the needle defines a channel, and wherein a distal portion of the needle defines an outlet in fluid communication with the channel;
wherein a radial outer surface of the introducer portion defines a radial opening in fluid communication with a gap of the introducer portion, wherein the medical device is configured to be transitioned from a first configuration to a second configuration, wherein, in the first configuration, the distal portion of the needle is within the first lumen, wherein, in the second configuration, the distal portion of the needle extends out of a distal opening of the first lumen, through the gap, and through the radial opening, and wherein, in the second configuration, the second longitudinal axis intersects the needle.

15. The medical device of claim 14, wherein a bridge longitudinally spans the gap.

16. The medical device of claim 15, wherein the bridge at least partially defines the radial opening.

17. The medical device of claim 14, wherein a cross-section of the introducer portion perpendicular to the second longitudinal axis, and including the first lumen and the second lumen, includes a first curved portion and a second curved portion, and wherein the first curved portion has a different radius of curvature than the second curved portion.

18. The medical device of claim 17, wherein the cross-section further includes first and second straight sides extending between the first curved portion and the second curved portion.

19. The medical device of claim 14, wherein the distal tip of the introducer portion is distal to the gap, and the second longitudinal axis passes through the gap.

* * * * *